United States Patent
Gauvry et al.

(10) Patent No.: US 8,822,466 B2
(45) Date of Patent: Sep. 2, 2014

(54) ISOXAZOLE DERIVATIVES

(75) Inventors: Noëlle Gauvry, Kembs (FR); Steve Nanchen, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/004,307

(22) PCT Filed: Mar. 9, 2012

(86) PCT No.: PCT/EP2012/054161
§ 371 (c)(1),
(2), (4) Date: Sep. 10, 2013

(87) PCT Pub. No.: WO2012/120135
PCT Pub. Date: Sep. 13, 2012

(65) Prior Publication Data
US 2013/0345221 A1    Dec. 26, 2013

(30) Foreign Application Priority Data
Mar. 10, 2011    (CH) ................... 00407/11

(51) Int. Cl.
| C07D 413/04 | (2006.01) |
| C07D 413/14 | (2006.01) |
| C07D 417/14 | (2006.01) |

(52) U.S. Cl.
CPC ............ *C07D 413/04* (2013.01); *C07D 413/14* (2013.01); *C07D 417/14* (2013.01)
USPC ........ 514/236.8; 514/256; 514/326; 514/340; 514/365; 514/378; 544/137; 544/333; 546/209; 546/272.1; 548/200; 548/240

(58) Field of Classification Search
None
See application file for complete search history.

(56) References Cited

FOREIGN PATENT DOCUMENTS

| WO | 2010070068 | 6/2010 |
| WO | 2011157748 | 12/2011 |

*Primary Examiner* — Alicia L Otton
(74) *Attorney, Agent, or Firm* — Ann R. Pokalsky; Dilworth & Barrese, LLP

(57) ABSTRACT

The invention relates to new isoxazoline compounds of formula

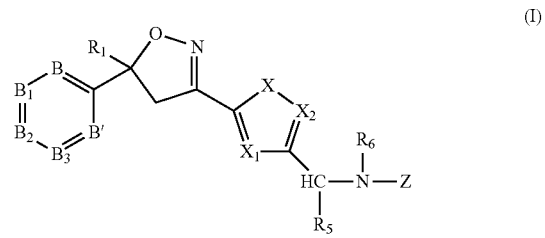

(I)

wherein the variables have the meaning as indicated in the claims; in free form and in salt form; and optionally the enantiomers and geometrical isomers thereof. The compounds of formula (I) are useful in the control of parasites, in particular ectoparasites, in and on vertebrates.

21 Claims, No Drawings

ISOXAZOLE DERIVATIVES

This application is a 371 application of PCT/EP2012/054161, filed Mar. 9, 2012, the contents of which are incorporated by reference herein.

FIELD OF THE INVENTION

This invention relates to novel isoxaolines, their N-oxides. S-oxides and salts, processes for their manufacture, their use in the control of ectoparasites, especially insects and acari, on non-human animals, especially productive livestock and domestic animals, and furthermore pesticidal compositions which contain one or more of these compounds.

BACKGROUND OF THE INVENTION

PCT Patent Publication WO 2007/075459 discloses isoxazoline derivatives of Formula (A) as plant insecticides

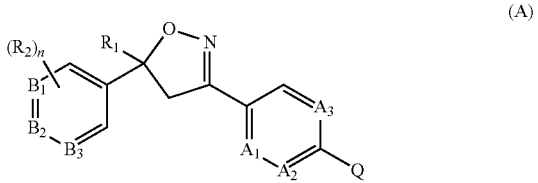

wherein, inter alia, each of $A_1$, $A_2$, and $B_1$-$B_3$ are $C(R_3)$, $A_3$ is N, $R_1$ is haloalkyl and Q is a heterocyclic radical.

The compounds are mainly used in the control of invertebrate pests in agronomic environments. Many products are commercially available for these purposes, but the need continues for new compounds that are more effective, less costly, less toxic, environmentally safer or have different modes of action. It now has been surprisingly found that novel derivatives with a modified heterocyclic side chain have superior properties in the control of pests.

SUMMARY OF THE INVENTION

This present invention is directed to a compound of formula

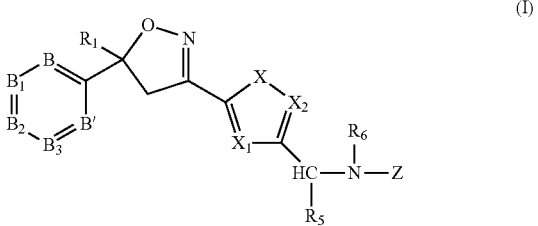

including all geometric and stereoisomers, N-oxides, S-oxides and salts thereof, and compositions containing them and their use for controlling parasites, wherein
X is $S(O)_m$, O or $NR_5'$ and $X_1$ and $X_2$ are each independently of the other $CR_3$ or N,
m is an integer from to 2;
$R_5'$ is H, $C_1$-$C_6$-alkyl, $C_1$-$C_6$-haloalkyl, $C_1$-$C_6$-alkylcarbonyl or $C_1$-$C_6$-alkoxycarbonyl;
each $R_3$ is independently H, halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkyl-sulfinyl, $C_1$-$C_6$-haloalkylsulfinyl, $C_1$-$C_6$-alkylsulfonyl, $C_1$-$C_6$-haloalkylsulfonyl, amino, N-mono- or N,N-di-$C_1$-$C_6$-alkylamino, $C_1$-$C_6$-alkoxycarbonyl, cyano, nitro or unsubstituted or halogen-, $C_1$-$C_6$-alkyl-, $C_1$-$C_6$-haloalkyl-, $C_1$-$C_6$-alkoxy-, $C_1$-$C_3$-haloalkoxy-, amino-, cyano- or nitro-substituted phenyl, pyridyl or pyrimidyl;
B and B' are each independently a group $CR_2'$;
$B_1$, $B_2$ and $B_3$ are each independently selected from the group consisting of $CR_2'$ and N;
each $R_2'$ is independently of the other H or $R_2$;
each $R_2$ is independently halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_3$-haloalkylthio, $C_1$-$C_6$-alkylsulfinyl, $C_1$-$C_6$-haloalkylsulfinyl, $C_1$-$C_8$-alkylsulfonyl, $C_1$-$C_6$-haloalkylsulfonyl, N-mono- or N,N-di-$C_1$-$C_6$-alkylamino, $C_1$-$C_6$-alkoxycarbonyl, cyano (—CN) or nitro (—$NO_2$);
$R_1$ is $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl or $C_4$-$C_7$-cycloalkylalkyl, each unsubstituted or substituted with one or more substituents independently selected from $R_4$;
$R_4$ is halogen, hydroxy, $C_1$-$C_6$-alkoxy, $C_1$-$C_6$-alkylthio, $C_1$-$C_6$-alkylsulfinyl, $C_1$-$C_6$-alkylsulfonyl, cyano or nitro;
$R_5$ is H, $C_1$-$C_6$-alkyl $C_1$-$C_6$-haloalkyl, halogen or cyano; or $R_5$ and $X_2$ together with the intermediate C-atoms for a 5- or 6-membered carbocyclic ring; or $R_5$ and $X_1$ together with the intermediate C-atoms form a 5- or 6-membered carbocyclic ring;
$R_6$ is H; $C_1$-$C_6$-alkyl, which is unsubstituted or substituted by $C_1$-$C_4$-alkoxy, cyano, phenyl, ethenyl or ethynyl; $C_2$-$C_7$-alkylcarbonyl; $C_2$-$C_7$-haloalkylcarbonyl; or $C_2$-$C_7$-alkoxycarbonyl;
Z is $C_1$-$C_6$-alkyl, a group —C(O)-Q, a group —C(S)-Q or a group —$S(O)_t$-Q; t is 1 or 2;
Q is $C_1$-$C_6$-alkoxy; $C_1$-$C_6$-haloalkoxy; $C_1$-$C_6$-alkylthio; $C_1$-$C_6$-haloalkylthio, $NR_7R_8$, $C(O)OR_7$; $C(O)R_7$; $C_1$-$C_6$-alkyl which is unsubstituted or substituted by $C_3$-$C_6$-cycloalkyl, halogen cyano, nitro, hydroxy $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $NHC(O)R_7$, $C_1$-$C_6$-alkoxycarbonyl, sulfonamido, N-mono- or N,N, di-$C_1$-$C_4$-alkylsulfonamido, $C(O)NR_7R_8$, $C_2$-$C_6$-alkanoyl, unsubstituted or $C_1$-$C_2$-alkyl-, $C_1$-$C_2$-alkoxy-, $C_1$-$C_2$-alkoxy-, $C_1$-$C_2$-haloalkoxy-, halogen-, cyano- or $C_1$-$C_4$-alkoxycarbonyl-substituted $C_8$-$C_{10}$-aryl, or unsubstituted or $C_1$-$C_2$-alkyl-, $C_1$-$C_2$-haloalkyl-, $C_1$-$C_2$-alkoxy-, $C_1$-$C_2$-haloalkoxy-, halogen-, cyano- or $C_1$-$C_4$-alkoxycarbonyl-substituted 4- to 6-membered heterocyclyl; $C_2$-$C_6$-alkenyl; $C_2$-$C_6$-alkynyl; $C_3$-$C_6$-cycloalkyl which is unsubstituted or substituted by halogen, $C_1$-$C_2$-alkyl or $C_1$-$C_2$-haloalkyl; $C_6$-$C_{10}$-aryl unsubstituted or substituted by $C_1$-$C_2$-alkyl, $C_1$-$C_2$-haloalkyl, $C_1$-$C_2$-alkoxy, $C_1$-$C_2$-haloalkoxy, halogen, cyano or $C_1$-$C_4$-alkoxycarbonyl, or 4- to 6-membered heterocyclyl unsubstituted or substituted by $C_1$-$C_2$-alkyl, $C_1$-$C_2$-haloalkyl, $C_1$-$C_2$-alkoxy, $C_1$-$C_2$-haloalkoxy, halogen, cyano or $C_1$-$C_4$-alkoxycarbonyl; and
$R_7$ and $R_8$ are each independently of the other H, $C_1$-$C_6$-alkyl, $C_1$-$C_6$-haloalkyl, unsubstituted or $C_1$-$C_4$-alkyl-substituted $C_3$-$C_6$-cycloalkyl. $C_2$-$C_6$-alkenyl or $C_2$-$C_6$-alkynyl.

This invention also provides a composition comprising a compound of formula (I), an N-oxide or a salt thereof, and at least one additional component selected from the group consisting of a surfactant, a solid diluent and a liquid diluent.

In one embodiment, this invention also provides a composition for controlling parasites, in particular ectoparasites, comprising a biologically effective amount of a compound of formula (I), an N-oxide, S-oxide or a salt thereof, and at least one additional component selected from the group consisting of a surfactant, a solid diluent and a liquid diluent, said composition optionally further comprising a biologically effective amount of at least one additional biologically active compound or agent.

This invention further provides the composition described above in the form of a bait composition wherein the solid diluent and/or the liquid diluent comprises one or more food materials, said composition optionally comprising an attractant and/or a humectant.

This invention further provides a trap device for controlling parasites, in particular ectoparasites, comprising said bait composition and a housing adapted to receive said bait composition, wherein the housing has at least one opening sized to permit the parasites to pass through the opening. so the invertebrate pest can gain access to said bait composition from a location outside the housing, and wherein the housing is further adapted to be placed in or near a locus of potential or known activity for the parasites pest.

This invention also provides a method for controlling parasites comprising contacting the parasites or their environment with a biologically effective amount of a compound of formula (I), an N-oxide, S-oxide or a salt thereof, (e.g., as a composition described herein). This invention also relates to such method wherein the parasites or their environment are contacted with a composition comprising a biologically effective amount of a compound of formula (I), an N-oxide, S-oxide or a salt thereof, and at least one additional component selected from the group consisting of a surfactant, a solid diluent and a liquid diluent, said composition optionally further comprising a biologically effective amount of at least one additional biologically active compound or agent.

This invention also provides a composition for protecting an animal from an parasitic pest comprising a parasiticidally effective amount of a compound of formula (I) an N-oxide or a salt thereof, and at least one carrier. The present invention further provides the composition described above in a form for oral administration. This invention also provides a method for protecting an animal from a parasitic pest comprising administering to the animal a parasiticidally effective amount of a compound of formula (I), an N-oxide or a salt thereof.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers.

The radical (alk) denotes, for example, straight-chain or branched $C_1$-$C_8$-alkylene, for example methylene, 1,1- or 1,2-ethylene or straight-chain or branched propylene, butylene, pentylene or hexylene. (alk) is preferably straight-chain or branched $C_1$-$C_4$-alkylene, more preferably $C_1$-$C_2$-alkylene, most preferably methylene, or 1,2-ethylene and in particular methylene.

"Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl.

"Alkynyl" includes straight-chain or branched alkynes such as ethynyl, 1-propynyl, 2-propynyl and the different butynyl, pentynyl and hexynyl isomers, "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers, "Alkylthio" includes branched or straight-chain alkylthio moieties such as methylthio, ethylthio, and the different propylthio, butylthio, pentylthio and hexylthio isomers.

"Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers.

Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers.

"N-alkylamino", "N,N-di-alkyamino" and the like, are defined analogously to the above examples.

"Cycloalkyl" includes, for example, cyclopropyl, cyclobutyl, cycopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropyl ethyl, cyclopentylethyl, and other cycloalkyl moieties bonded to straight-chain or branched alkyl groups.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$—, $ClCH_2$—, $CF_3CH_2$— and $CF_3CCl_2$—. The terms "halocycloalkyl", "haloalkoxy", "haloalkylthio", and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—.

"Alkylcarbonyl" denotes a straight-chain or branched alkyl moieties bonded to a C(=O) moiety. Examples of "alkylcarbonyl" include $CH_3C(=O)$—, $CH_3CH_2CH_2C(=O)$— and $(CH_3)_2CHC(=O)$—. Examples of "alkoxycarbonyl" include $CH_3C(=O)$—, $CH_3CH_2OC(=O)$, $CH_3CH_2CH_2C(=O)$—, $(CH_3)_2CHOC(=O)$— and the different butoxy- or pentoxycarbonyl isomers, for example tert.-butoxycarbonyl (Boc).

The total number of carbon atoms in a substituent group is indicated by the "$C_i$-$C_j$" prefix where i and j are integers. For example, $C_1$-$C_4$ alkylsulfonyl designates methylsulfonyl through butylsulfonyl; $C_2$-alkoxyalkyl designates $CH_3OCH_2$; $C_3$-alkoxyalkyl designates, for example, $CH_3CH(OCH_3)$, $CH_3OCH_2CH_2$ or $CH_3CH_2OCH_2$; and $C_4$-alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$—.

When a compound is substituted with a substituent bearing a subscript that indicates the number of said substituents can exceed 1, said substituents (when they exceed 1) are independently selected from the group of defined substituents, e.g., $(R_2)_n$, n is 1 or 2. "Aromatic" indicates that each of the ring atoms is essentially in the same plane and has ap-orbital perpendicular to the ring plane, and in which (4n+2) π electrons, where n is a positive integer, are associated with the ring to comply with Hückers rule.

The terms "heterocyclic ring", "heterocycle" or "heterocyclyl" denote a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring", "aromatic heterocyclic ring". Unless otherwise indicated, heterocyclic rings and ring systems can be attached through any available carbon or nitrogen by replacement of a hydrogen on said carbon or nitrogen.

When Q is a 4- to 6-membered nitrogen-containing heterocyclic ring, it may be attached to the remainder of formula (I) though any available carbon or nitrogen ring atom, unless otherwise described.

Each $R_2$ is independently of the other preferably halogen, $C_1$-$C_6$-haloalkyl, $C_1$-$C_6$ haloalkoxy or cyano, more preferably halogen, $CF_3$, $OCF_3$ or cyano, especially halogen, for example chlorine or fluorine, and in particular chlorine.

B and B' are each independently preferably a radical CH or $CR_2$, wherein $R_2$ is halogen, in particular each a radical CH.

$B_1$, $B_2$ and $B_3$ are each independently of the other preferably a group $CR_2'$, wherein $R_2'$ is H or $R_2$, and for $R_2$ the above-given meanings and preferences apply. One preferred embodiment relates to a compound of formula (I), wherein one of the radicals $B_1$, $B_2$ and $B_3$ is CH and the two other ones are each independently a radical $CR_2$, wherein $R_2$ is halogen, for example chlorine or fluorine, and in particular chlorine; within this embodiment it is particularly preferred, that $B_2$ is CH and $B_1$ and $B_3$ are each independently CCl or CF. Another preferred embodiment relates to a compound of formula (I), wherein all three radicals $B_1$, $B_2$ and $B_3$ are each independently a radical $CR_2$, wherein $R_2$ is halogen, for example chlorine or fluorine, and in particular each chlorine.

$R_4$ is preferably halogen, $C_1$-$C_2$-alkoxy, cyano or nitro, more preferably halogen, cyano or nitro, and in particular halogen.

$R_1$ is preferably $C_1$-$C_6$-alkyl optionally substituted with one or more substituents independently selected from $R_4$, more preferably $C_1$-$C_3$-alkyl optionally substituted with halogen, even more preferably halo-$C_1$-$C_3$-alkyl, especially preferably $C_1$-$C_2$-alkyl substituted with F, and in particular $CF_3$.

Each $R_3$ is independently of the other preferably H, halogen, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, N-mono- or N,N-di-$C_1$-$C_6$-alkylamino, cyano or nitro, more preferably H, halogen, $C_1$-$C_2$-alkyl $C_1$-$C_2$-haloalkyl, cyclopropyl, $C_1$-$C_2$-alkoxy, cyano or nitro, even more preferably H, halogen, $C_1$-$C_2$-alkyl, $C_1$-$C_2$-alkoxy, cyano or nitro, and in particular H or $C_1$-$C_2$-alkyl.

According to a further preferred embodiment of the invention, $R_3$ is phenyl, pyridyl or pyrimidyl, which is unsubstituted or substituted by halogen, $C_1$-$C_6$-alkyl, $C_1$-$C_6$-haloalkyl, $C_1$-$C_6$-alkoxy, $C_1$-$C_6$-haloalkoxy, amino, cyano or nitro; preferably phenyl, pyridyl or pyrite which is unsubstituted or substituted by fluorine, chlorine, methyl, trifluoromethyl, methoxy, trifluoromethoxy, amino, cyano or nitro; and in particular phenyl which is unsubstituted or substituted by chlorine, fluorine, methyl or trifluoromethyl.

$X_1$ or $X_2$ are each independently preferably a group $CR_3$, wherein for $R_3$ the above-given meanings and preferences apply. $X_1$ or $X_2$ are each independently most preferably a radical $CR_3$, wherein $R_3$ is H or $C_1$-$C_2$-alkyl. $X_1$ is particularly preferably CH and $X_2$ is particularly preferably $C(C_1$-$C_2$-alkyl), especially $C(CH_3)$.

$R_5'$ is preferably H or $C_1$-$C_2$-alkyl. m is, for example 0, 1 or 2, in particular 0.

X is preferably $S(O)_m$ or O, wherein for m the above-given meanings and preferences apply, in particular S or O, and especially S. A further particularly preferred meaning of X is O.

According to one embodiment of the invention X is S(O), or O, m is 0, 1 or 2, one of $X_1$ and $X_2$ is $CR_3$ and the other one is N or independently another $CR_3$, and $R_3$ is H or $C_1$-$C_2$-alkyl.

Preferably X is S or O, and $X_1$ and $X_2$ are each independently a radical $CR_3$, wherein for $R_3$ the above given meanings and preferences apply. More preferably, X is S or O, $X_1$ is CH, and $X_2$ is $CR_3$, wherein for $R_3$ the above given meanings and preferences apply. Most preferably X is S, $X_1$ is CH and $X_2$ is $C(C_1$-$C_2$-alkyl) or in particular $C(CH_3)$. Also very preferably X is O, $X_1$ is CH and $X_2$ is $C(C_1$-$C_2$-alkyl) or in particular $C(CH_3)$.

$R_5$ is preferably H or $C_1$-$C_2$-alkyl or cyano, more preferably H or methyl, and in particular H.

According to a further embodiment of the invention, $R_5$, $X_1$ or $X_2$ and the intermediate C-atoms form a saturated, partially saturated or unsaturated 5- or 6-membered carbocyclic ring. The compounds of this embodiment are, for example, of the formula

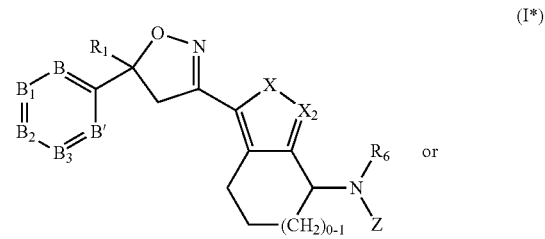

(I*)

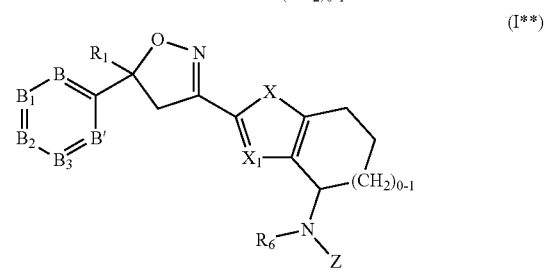

(I**)

wherein the variables each have the meanings and preferences as indicated above and below.

$R_6$ is preferably H, cyanomethyl, benzyl, propenyl or propynyl, particular H.

Z is preferably a group —C(O)-Q or a group —S(O)$_t$-Q, in particular a group —C(O)-Q, wherein t is an integer of 0, 1 or 2, in particular 2, and for Q each the above given meanings and the preferences as given below apply.

Q as alkoxy is preferably $C_1$-$C_4$-alkoxy, in particular methoxy, ethoxy or n- or isopropoxy.

Q as haloalkoxy is preferably $C_1$-$C_2$-haloalkyl, in particular 2,2,2-trifluoroethoxy or trifluoromethoxy.

Q as alkylthio is preferably methylthio or ethylthio.

Q as haloalkylthio is preferably trifluoromethylthio.

Q as radical —$NR_7R_8$ is preferably, N-mono- or N,N-di-$C_1$-$C_4$-alkylamino, N—$C_1$-$C_2$-halo alkylamino, N—$C_3$-$C_6$- cycloalkylamino or N—$C_1$-$C_2$-alkyl,N—$C_3$-$C_6$-cycloalkylamino, in particular N-mono- or N,N-di-$C_1$-$C_2$-alkylamino or N—$C_3$-$C_6$-cycloalkylamino.

If Q is $C_1$-$C_6$-alkyl substituted by $C_6$-$C_{10}$-aryl, said aryl is, for example phenyl, naphthyl, tetrahydronaphthyl, indanyl or indenyl, in particular phenyl. The $C_6$-$C_{10}$-aryl is each unsubstituted or substituted by one or more same or different substituents, for example selected from the group consisting of $C_1$-$C_2$-alkyl, $C_1$-$C_2$-haloalkyl, $C_1$-$C_2$-alkoxy, $C_1$-$C_2$-haloalkoxy, halogen, cyano and $C_1$-$C_4$-alkoxycarbonyl. A preferred aryl substituent of the $C_1$-$C_6$-alkyl radical Q is phenyl, which is substituted by 1 to 3, in particular 1 or 2, same or different substituents selected from the group consisting of halogen, $C_1$-$C_2$-alkyl, $C_1$-$C_2$-haloalkyl, $C_1$-$C_2$-alkoxy, $C_1$-$C_2$-haloalkoxy, cyano and $C_1$-$C_4$-alkoxycarbonyl.

If Q is $C_1$-$C_6$-alkyl substituted by 4- to 6-membered heterocyclyl, said heterocyclyl is, for example, a heteroaromatic or heteroaliphatic ring radical which is unsubstituted or further substituted.

Preferred substituents of the heterocyclyl are, for example, halogen, $C_1$-$C_2$-alkyl, $C_1$-$C_2$-haloalkyl, $C_1$-$C_2$-alkoxy, $C_1$-$C_2$-haloalkoxy, cyano and $C_1$-$C_4$-alkoxycarbonyl.

A suitable heterocyclic substituent of the $C_1$-$C_6$-alkyl radical Q is, for example, a 5- or 6-membered heteroaromatic radical having from 1 to 4, preferably from 1 to 3 same or different heteroatoms selected from the group consisting of N, O and S, which is further unsubstituted or substituted by one or more substituents as defined above for heterocyclic rings including the preferences given therefore. The heteroaromatic radical is preferably substituted by 0 to 3, in particular 0, 1 or 2 substituents from the group as defined above.

Examples of a 5- or 6-membered heteroaromatic substituent of the $C_1$-$C_6$-alkyl radical Q include a thienyl, furyl, oxazolyl, thiazolyl, pyridyl or pyrimidinyl radical which is unsubstituted or substituted by $C_1$-$C_2$-alkyl, $C_1$-$C_2$-haloalkyl or $C_1$-$C_4$-alkoxycarbonyl. Especially preferred heteroaromatic substituents of the $C_1$-$C_6$-alkyl radical Q are 2-, 3- or 4-pyridyl, 2- or 4-pyrimidinyl, 2-thiazolyl or 2-thienyl.

A further suitable heterocyclic substituent of the $C_1$-$C_6$-alkyl radical Q is, for example, a 4- to 6-membered heteroaliphatic ring having from 1 to 4, preferably from 1 to 3 same or different heteroatoms selected from the group consisting of N, O and S, which is further unsubstituted or substituted by one or more substituents as defined before for heterocyclic rings including the preferences given therefore.

Examples of heteroaliphatic ring substituents of the $C_1$-$C_6$-alkyl radical Q include a thietanyl, for example thietan-3-yl, oxo-thietanyl, dioxo-thiethanyl, oxetanyl, for example oxetan-3-yl, azetidinyl, pyrrolidinyl, tetrahydrofuranyl, tetrahydrothiophenyl, piperidinyl, piperazinyl, morpholinyl, tetrahydropyranyl, thianyl, dioxanyl or dioxolanyl radical which is each unsubstituted or substituted by $C_1$-$C_2$-alkyl, $C_1$-$C_2$-haloalkyl or $C_1$-$C_4$-alkoxycarbonyl.

Preferred heteroaliphatic substituents of the $C_1$-$C_6$-alkyl radical Q include pyrrolidinyl, tetrahydrofuranyl, tetrahydrothiophenyl, piperidinyl, piperazinyl, morpholinyl, tetrahydropyranyl or thianyl which are each unsubstituted or substituted by $C_1$-$C_2$-alkyl, $C_1$-$C_2$-haloalkyl or $C_1$-$C_4$-alkoxycarbonyl, as well as dioxanyl or dioxolanyl and in particular pyrrolidine-1-yl, tetrahydrofuran-2-yl, tetrahydrofuran-3-yl, piperidine-1-yl, morpholine-4-yl, thiane-4-yl, 1,3-dioxan-2-yl and 1,3-dioxolan-2-yl, in particular tetrahydrofuran-2-yl, tetrahydrofuran-3-yl, morpholine-4-yl, thiane-4-yl and 1,3-dioxolan-2-yl.

Q as optionally substituted alkyl is preferably straight-chain or branched $C_1$-$C_4$-alkyl, which is each unsubstituted or substituted by $C_3$-$C_6$-cycloalkyl, halogen, cyano, $C_1$-$C_4$-alkoxy, $C_1$-$C_2$-haloalkoxy, $C_1$-$C_4$-alkylthio, $C_1$-$C_2$-haloalkylthio $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_2$-alkylcarbonylamino, $C_1$-$C_2$-haloalkyl-carbonylamino or dioxolanyl. Especially preferred alkyl radicals Q are straight-chain or branched $C_1$-$C_4$-alkyl or $C_1$-$C_4$-alkyl which is substituted by $C_3$-$C_4$-cycloalkyl, halogen, cyano, $C_1$-$C_2$-alkoxy, $C_1$-$C_2$-alkylthio, $C_1$-$C_2$-alkylsulfinyl, $C_1$-$C_2$-alkylsulfonyl, $C_1$-$C_2$-haloalkyl-carbonylamino or dioxolanyl. Particularly preferred alkyl radicals Q are straight-chain or branched $C_1$-$C_4$-alkyl, $C_1$-$C_4$-haloalkyl or $C_1$-$C_2$-alkyl which is substituted by cyano, $C_1$-$C_2$-alkoxy, $C_1$-$C_2$-alkylthio, $C_1$-$C_2$-alkylsulfonyl $C_1$-$C_2$-haloalkylcarbonylamino or 1,3-dioxolan-2yl.

Q as alkyl is especially preferred straight-chain or branched $C_1$-$C_4$-alkyl, $C_1$-$C_3$-haloalkyl, cyano-$C_1$-$C_2$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulfinyl-$C_1$-$C_2$-alkylsulfonyl-$C_1$-$C_2$-alkyl, $C_1$-$C_2$-haloalkylcarbonylamino-$C_1$-$C_2$-alkyl or 2-(1,3-dioxolan-2yl)-propyl.

A preferred alkenyl radical Q is $C_2$-$C_3$-alkenyl, in particular 2-propenyl. A preferred alkynyl radical Q is $C_2$-$C_3$-alkynyl, in particular 2-propynyl.

A preferred cycloalkyl radical Q is preferably cyclopropyl, cyclobutyl, cyclopentyl or cyclohexyl, which is in each case unsubstituted or substituted, for example by $C_1$-$C_2$-alkyl or halogen, in particular by one or more methyl groups. Q as $C_3$-$C_6$-cycloalkyl is preferably cyclopropyl or cyclobutyl.

If Q denotes $C_6$-$C_{10}$-aryl, the meanings and preferences as given before for the $C_6$-$C_{10}$-aryl substituent of the $C_1$-$C_6$-alkyl radical Q apply.

If Q denotes heterocyclyl, the meanings and preferences as given before for the heterocyclic substituent of the $C_1$-$C_6$-alkyl radical Q apply.

Q is preferably straight-chain or branched $C_1$-$C_4$-alkyl, which is each unsubstituted or substituted by $C_3$-$C_6$-cycloalkyl, halogen, cyano, hydroxy, $C_1$-$C_4$-alkoxy, $C_1$-$C_4$-haloalkoxy $C_1$-$C_4$-alkylthio, $C_1$-$C_4$-haloalkylthio, $C_1$-$C_4$-alkylsulfinyl, $C_1$-$C_4$-alkylsulfonyl, $C_1$-$C_2$-alkylcarbonylamino, $C_1$-$C_2$-haloalkylcarbonylamino or dioxolanyl unsubstituted or methyl-substituted $C_3$-$C_6$-cycloalkyl; phenyl, which is substituted or substituted by halogen, $C_1$-$C_2$-alkyl, $C_1$-$C_2$-haloalkyl, $C_1$-$C_2$-alkoxy, $C_1$-$C_2$-haloalkoxy, cyano or $C_1$-$C_4$-alkoxycarbonyl; thienyl, furyl, oxazolyl, thiazolyl, pyridyl or pyrimidinyl, which are each unsubstituted or substituted by $C_1$-$C_2$-alkyl, $C_1$-$C_2$-haloalkyl or $C_1$-$C_4$-alkoxycarbonyl; 1,3-dioxan-2-yl or 1,3-dioxolan-2-yl; or pyrrolidinyl, tetrahydrofuranyl, tetrahydrothiophenyl, piperidinyl, piperazinyl, morpholinyl, tetrahydropyranyl or thienyl which are each unsubstituted or substituted by $C_1$-$C_2$-alkyl, $C_1$-$C_2$-haloalkyl or $C_1$-$C_4$-alkoxycarbonyl.

Q is in particular straight-chain or branched $C_1$-$C_4$-alkyl, cyclopropyl, cyclobutyl, halo-$C_1$-$C_3$-alkyl, cyano-$C_1$-$C_2$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulfinyl-$C_1$-$C_2$-alkyl, $C_1$-$C_2$-alkylsulfonyl-$C_1$-$C_2$-alkyl, $C_1$-$C_2$-haloalkylcarbonylamino-$C_1$-$C_2$-alkyl, tetrahydrofuran-2-yl, tetrahydrofuran-3-yl or 2-(1,3-dioxolan-2yl)-n-propyl.

If Z is a group —S(Q)$_t$-Q, t is preferably an integer 2; in addition, all the meanings and preferences given above for Q apply. According to a preferred embodiment, Z is a group —S(O)$_t$-Q, t is 2 and Q is $C_1$-$C_4$-alkyl, in particular methyl or ethyl.

According to a preferred embodiment of the invention there is provided a compound of formula

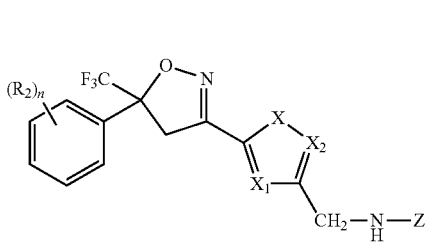

(Ia)

including all geometric and stereoisomers, N-oxides, S-oxides and salts thereof, wherein for $R_2$, X, $X_1$, $X_2$ and Z each the above-given meanings and preferences apply, and n is an integer of from 0 to 4, preferably of from 1 to 3, and in particular of 2 or 3.

In particular, n is an integer from 1 to 3; each $R_2$ is independently selected from the group consisting of halogen, $C_1$-$C_6$-haloalkyl, $C_1$-$C_6$-haloalkoxy and cyano; X is $S(O)_m$, O or $NR_5'$; m is an integer from 0 to 2; $R_5'$ is H or $C_1$-$C_2$-alkyl; one of $X_1$ and $X_2$ is $CR_3'$ and the other one is N or independently $CR_3'$; $R_3'$ is H or $C_1$-$C_2$-alkyl; Z is a group $S(O)_2$— $C_1$-$C_2$-alkyl or a group —C(O)-Q; and Q is straight-chain or branched $C_1$-$C_4$-alkyl, which is each unsubstituted or substituted by $C_3$-$C_6$-cycloalkyl, halogen, cyano, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-alkylsulfonyl, $C_1$-$C_2$-alkylcarbonylamino, $C_1$-$C_2$-haloalkylcarbonylamino or dioxanyl; unsubstituted or methyl-substituted $C_3$-$C_6$-cycloalkyl; phenyl, which is unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano or $C_1$-$C_4$-alkoxycarbonyl; furyl, thienyl, oxazolyl, thiazolyl pyridyl or pyrimidinyl, which are each unsubstituted or substituted by $C_1$-$C_2$-alkyl, $C_1$-$C_2$-haloalkyl or $C_1$-$C_4$-alkoxycarbonyl; or pyrrolidinyl, tetrahydrofuranyl, tetrahydrothiophenyl, piperidinyl piperazinyl, morpholinyl, tetrahydropyranyl or thianyl which is each unsubstituted or substituted by $C_1$-$C_2$-alkyl, $C_1$-$C_2$-haloalkyl or $C_1$-$C_4$-alkoxycarbonyl.

According to a particularly preferred embodiment of the invention there is provided a compound of formula

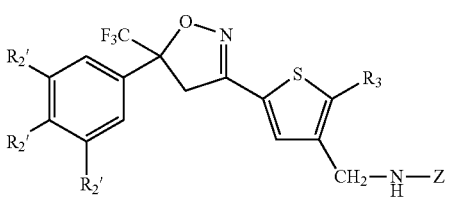

(Ib)

including all geometric and stereoisomers, N-oxides, and salts thereof, wherein the radicals $R_2'$ are each in of the other H, halogen or trifluoromethyl, subject to the proviso that at least 2 radicals $R_2'$ are not H; $R_3$ is hydrogen or methyl; Z is a radical —C(O)-Q; and Q is straight-chain or branched $C_1$-$C_4$-alkyl, cyclopropyl, cyclobutyl, $C_1$-$C_3$-haloalkyl, cyano-$C_1$-$C_2$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulfinyl-$C_1$-$C_2$-alkyl, $C_1$-$C_2$-alkylsulfonyl-$C_1$-$C_2$-alkyl, $C_1$-$C_2$-haloalkylcarbonylamino-$C_1$-$C_2$-alkyl, tetrahydrofuranyl or 2-(1,3-dioxolan-2yl)-n-propyl.

Particularly preferred members of this embodiment are N-{5-[5-(3,5-dichloro-phenyl)-5-trifluoromethyl-4,5-dihydro-isoxazol-3-yl]-2-methyl-thiophen-3-ylmethyl}-propionamide; N-{5-[5-(3,4,5-trichloro-phenyl)-5-trifluoromethyl-4,5-dihydro-isoxazol-3-yl]-2-methyl-thiophen-3-ylmethyl}-propionamide; cyclopropanecarboxylic acid {2-methyl-5-[5-(3,5-dichloro-phenyl)-5-trifluoromethyl-4,5-di-hydro-isoxazol-3-yl]-thiophen-3-ylmethyl}-amide, cyclopropanecarboxylic acid {2-methyl-5-[5-(3,4,5-trichloro-phenyl)-5-trifluoromethyl-4,5-di-hydro-isoxazol-3-yl]-thiophen-3-ylmethyl}-amide; tetrahydro-furan-3-carboxylic acid {2-methyl-5-[5-{3,5-dichloro-phenyl)-5-trifluoromethyl-4,5-dihydro-isoxazol-3-yl]-thiophen-3-ylmethyl}-amide; and tetrahydro-furan-3-carboxylic acid {2-methyl-5-[5-(3,4,5-trichloro-phenyl)-5-trifluoromethyl-4,5-dihydro-isoxazol-3-yl]-thiophen-3-ylmethyl}-amide.

According to a further particularly preferred embodiment of the invention there is provided a compound of formula

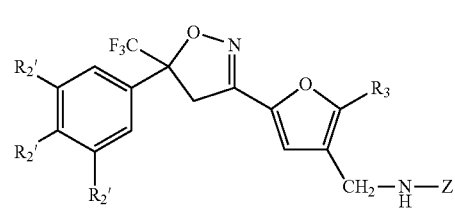

(Ic)

including all geometric and stereoisomers, N-oxides, and salts thereof, wherein the radicals $R_2'$ are each independently of the other H, halogen or trifluoromethyl, subject to the proviso that at least 2 radicals $R_2'$ are not H; $R_3$ is hydrogen or methyl; Z is a radical —C(O)-Q; and Q is straight-chain or branched $C_1$-$C_4$-alkyl, cyclopropyl, cyclobutyl, $C_1$-$C_3$-haloalkyl, cyano-$C_1$-$C_2$-alkyl, $C_1$-$C_2$-alkoxy-$C_1$-$C_2$-alkyl, $C_1$-$C_2$-alkylthio-$C_1$-$C_2$-alkyl, alkyl, $C_1$-$C_2$-alkylsulfonyl-$C_1$-$C_2$-alkyl, $C_1$-$C_2$-haloalkylcarbonylamino-$C_1$-$C_2$-alkyl, tetrahydrofuranyl or 2-(1,3-dioxolan-2-yl)-n-propyl.

Particularly preferred members of this embodiment are N-{5-[5-(3,5-dichloro-phenyl)-5-trifluoromethyl-4,5-dihydro-isoxazol-3-yl]-2-methyl-furan-3-ylmethyl}-propionamide; N-{5-[5-(3,4,5-trichloro-phenyl)-5-trifluoromethyl-4,5-dihydro-isoxazol-3-yl]-2-methyl-furan-3-ylmethyl}-propionamide; cyclopropanecarboxylic acid {2-methyl-5-[5-(3,5-dichloro-phenyl)-5-trifluoromethyl-4,5-di-hydro-isoxazol-3-yl]-furan-3-ylmethyl}-amide; cyclopropanecarboxylic acid {2-methyl-5-[5-(3,4,5-trichloro-phenyl)-5-trifluoromethyl-4,5-di-hydro-isoxazol-3-yl]-furan-3-ylmethyl}-amide; tetrahydro-furan-3-carboxylic acid {2-methyl-5-[5-(3,5-dichloro-phenyl)-5-trifluoromethyl-4,5-dihydro-isoxazol-3-yl]-furan-3-ylmethyl}-amide, and tetrahydro-furan-3-carboxylic acid {2-methyl-5-[5-(3,4,5-trichloro-phenyl)-5-trifluoromethyl-4,5-dihydro-isoxazol-3-yl]-furan-3-ylmethyl}-amide.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers, or as an optically active form.

One skilled in the art will appreciate that not all nitrogen containing heterocyclic rings can form N-oxides since the nitrogen requires an available lone pair for oxidation to the oxide; one skilled in the art will recognize those nitrogen containing heterocyclic rings which can form N-oxides. One skilled in the art will also recognize that tertiary amines can for N-oxides. Synthetic methods for the preparation of N-oxides of heterocyclic rings and tertiary amines are very well known by one skilled in the art including the oxidation of heterocyclic rings and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyl dioxirane These methods for the preparation of N-oxides have been extensively described and reviewed in the literature. The manufacture of suitable S-oxides may be performed in an analogous manner using, for example, the same kind of oxidants as mentioned above for the N-oxides.

One skilled in the art recognizes that because of the environment and under physiological conditions salts of chemical compounds are in equilibrium with their corresponding non-salt forms, salts share the biological utility of the nonsalt forms. Thus a wide variety of salts of the compounds of formula (I) are useful for control of invertebrate pests (i.e. are veterinarily or agriculturally suitable). The salts of the compounds of formula (I) include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of formula (I) contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from formula (I), N-oxides and veterinary acceptable and agriculturally suitable salts thereof.

The compounds of the present invention may be prepared, for example, by reacting a compound of formula

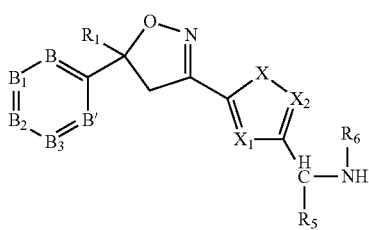

(II)

with a compound of formula

Z-LG (III), wherein Z is $C_1$-$C_6$-alkyl or a radical C(O)-Q or S(O)$_t$-Q, LG is a leaving group, for example halogen, hydroxy or $C_1$-$C_4$-alkoxy, and the further variables are defined as described above, and, if $R_6$ is hydrogen, optionally further reacting the resulting compound of formula

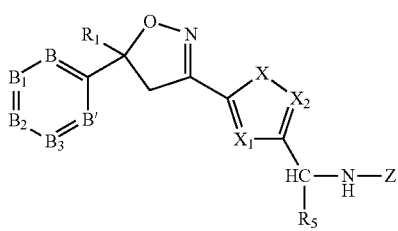

(I')

with a compound of formula $R_6$-LG' (IV), wherein $R_6$ is as defined above with the exception of H, and LG' is a leaving group, for example halogen. The reactions of the compounds of formula (II) and (III) on the one hand and of formula (I') and (IV) on the other hand each may be performed by methods known per se, for example, from textbooks of Organic Chemistry.

A further synthetic route for the manufacture of the compounds of formula (I') wherein Z is a radical C(O)Q comprises subjecting a compound of formula

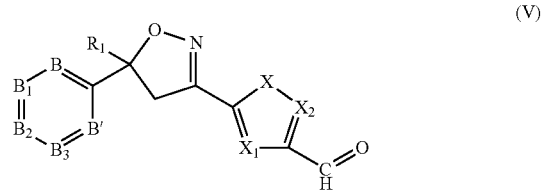

(V)

to a triethylsilane-promoted reductive amination with a compound of formula

(VI)

wherein Q is as defined above. The reaction of the compounds of formula (V) and (VI) takes place, for example, at elevated temperature in an inert solvent such as toluene or the like in the presence of a strong acid, for example trifluoroacetic acid. Typical reaction conditions can be found in Tetrahedron Letters 1999, 2295.

The compounds of formula (V) may be prepared from a compound of formula

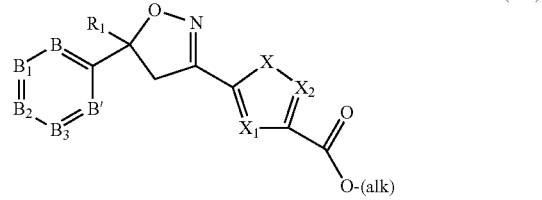

(VII)

wherein (alk) is, for example, straight-chain or branched $C_1$-$C_6$-alkyl, by converting said compound to the respective aldehyde of formula (V). It may be advisable to first reduce the compound of formula (VII) to the respective alcohol (~$CH_2$—OH) and then oxidizing said alcohol to the aldehyde of formula (V), for example, with $MnO_2$.

The compounds of formula (VII) may be prepared from a compound of formula

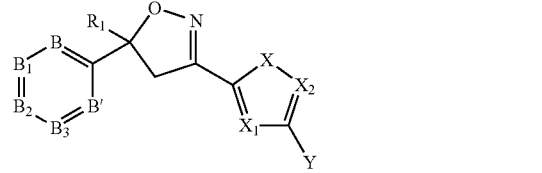

(VIII)

wherein Y is an halogen, in particular bromine or iodine. The reaction of a compound of formula (VIII) takes place, for example, by lithium halogen exchange or by converting compound (VIII) into a Grignard reagent and further reaction with alkyloyanoformate or $CO_2$ and additional treatment with an alcohol (alk)-OH.

Another process for the preparation of compounds of the formula (VII) includes the alkoxycarbonylation of an arylbromide oder iodide of the above formula (VIII), wherein V is Br or I, with an alcohol (alk)-OH and carbon monoxide. The reaction is typically carried out in the presence of a palladium catalyst under CO atmosphere. Many catalysts are useful for this type of transformation; a typical catalyst is tetrakis(triphenylphosphine)palladium(0). Solvents such as 1,2-dimethoxyethane, N,N-dimethylacetamide or toluene are suitable. The method can be conducted over a wide range of temperatures, for example from about 25° C. to about 150° C., especially from 60 to 110° C.

The compounds of formula (VII) and (VIII) may also be prepared, for example, by cycloaddition of a compound of formula

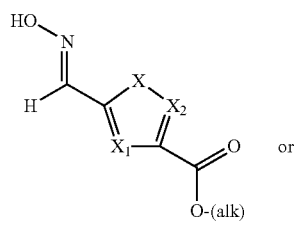

(IX)

with a nitrile oxide derived from an oxime of formula

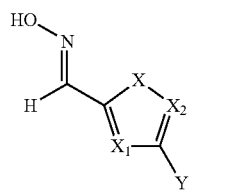

(Xa)

or (Xb)

wherein B, B', $B_1$-$B_3$, $R_1$, X, $X_1$, $X_2$, Y and (alk) each have the above-given meaning to yield a compound of formula (VII) or (VIII) respectively.

The reaction typically proceeds through the intermediacy of an in situ generated hydroxamyl chloride. In a typical procedure a chlorinating reagent such as sodium hypochlorite, N-chlorosuccinimide, or chloramine-T is combined with the oxime in the presence of the styrene. Depending on the conditions amine bases such as pyridine or triethylamine may be necessary. The reaction can be run in a wide variety of solvents including tetrahydrofuran, diethyl ether, methylene chloride, dioxane, and toluene with optimum temperatures ranging from morn temperature to the reflux temperature of the solvent.

The compounds of formula (IX) are known, for example, from WO 2007/079162 or may be prepared in analogy to the methods disclosed therein. Likewise, the compounds of formula (Xa) and (b) are known or may be prepared by methods known per se.

The compounds of formula (VII) and (VIII), respectively, may also be prepared by a process in analogy of WO2009/025983, wherein a compound of formula (XIa) below is contacted with hydroxylamine and a base to form an isoxazole of formula (XI)

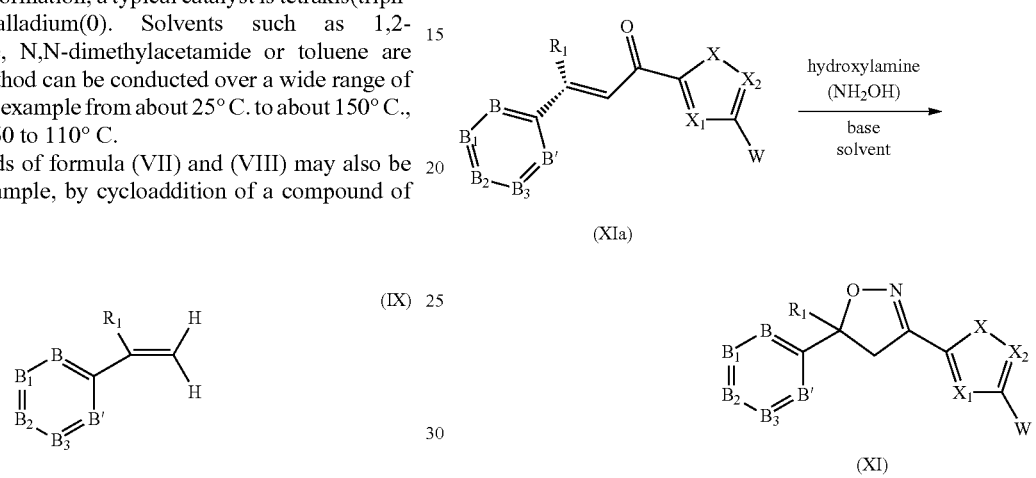

wherein $B_1$-$B_3$, $R_1$, $R_2$ X, $X_1$, $X_2$ and n each have the above-given meaning and W is a radical —C(O)—O(alk) or Y. The reaction may be performed as described in WO2009/025983 on pages 29-31. In addition, synthetic routes to prepare the intermediate of formula (XIa) are likewise disclosed in WO2009/025983 on pages 31-34.

The compounds of formula (II) above may be prepared, for example, from a compound of formula (VIII) above, wherein Y is halogen, in particular Br, by suitable conversion of the halogen group Y to a cyano group Y and its subsequent reduction to an amino group —$CH_2NH_2$.

Another synthetic route for the preparation of the compounds of formulation (II), wherein. $R_5$ and $R_6$ are hydrogen comprises reacting an aldehyde compound of the formula (V) with a compound of formula.

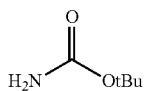

The resulting compound is then deprotected by methods known per se in the literature, for example with a strong acid like trifluoroacetic acid to form an amine of formula (II) wherein $R_5$ and $R_6$ are hydrogen.

A further synthetic route for the preparation of the compounds of formula (II) comprises subjecting an aldehyde compound of the formula (V) to a Grignard reaction with a compound $R_5$MgHal, wherein $R_5$ is as defined above and Hal is halogen, in particular bromine, and converting the OH group in the resulting compound of the formula

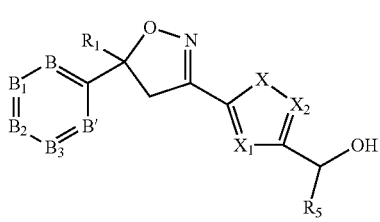

to the respective amino compound by methods known per se.

The reaction of an aldehyde compound of formula (V) in a medium of an inorganic cyanide, for example KCN, aqueous ammonia and ammonium chloride yields a compound of formula (XII) above, wherein $R_5$ is cyano, which in turn may be further converted to the corresponding aminomethyl group.

The compounds of the formula (III) above are known and commercially available in park or may be prepared according to processes well-known in the art.

The compounds of the formula (I) according to the invention are notable for their broad activity spectrum and are valuable active ingredients for use in pest control. They are particularly suitable in the control of ectoparasites and to a certain extent also for controlling endoparasites on and in animals and in the hygiene field, whilst being well tolerated by vertebrates such as warm-blooded animals and fishes.

Animals in the context of the invention are understood to include vertebrates. The term vertebrate in this context is understood to comprise, for example fishes, amphibians, reptiles, birds, and mammals including humans. One preferred group of vertebrates according to the invention comprises warm-blooded animals including farm animals, such as cattle, horses, pigs, sheep and goats, poultry such as chickens, turkeys, guinea fowls and geese, fur-bearing animals such as mink, foxes, chinchillas, rabbits and the like, as well as companion animals such as ferrets, guinea pigs, rats, hamster, cats and dogs, and also humans. A further group of preferred vertebrates according to the invention comprises fishes including salmons.

In the context of the present invention, ectoparasites are understood to be in particular insects, scan (mites and ticks), and crustaceans (sea lice). These include insects of the following orders: Lepidoptera, Coleoptera, Homoptera, Hemiptera, Heteroptera, Diptera, Dictyoptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga carnaria, Lucilia cuprina, Lucilia sericate, Hypoderma bovis, Hypoderma lineatum, Chrysomyia chloropyga, Dermatobia hominis, Cochliomyia hominivorax, Gasterophilus intestinalis, Oestrus ovis*, biting flies such as *Haematobia irritans irritans, Haematobia irritans exigua, Stomoxys oalcitrans*, horse-flies (Tabanids) with the subfamilies of Tabanidae such as *Haematopota* spp. (e.g. *Haematopota pluvialis*) and *Tabanus* spp, (e.g. *Tabanus nigrovittatus*) and Chrysopsinae such as *Chrysops* spp. (e.g. *Chrysops caecutiens*); Hippoboscids such as *Melophagus ovinus* (sheep ked); tsetse flies, such as *Glossinia* spp,; other biting insects like midges, such as Ceratopogonidae (biting midges), Simullidae (Blackflies), Psychodidae (Sandflies); but also blood-sucking insects, for example mosquitoes, such as *Anopheles* spp, *Aedes spp* and *Culex* spp, fleas, such as *Ctenocephalides felis* and *Ctenocephalides canis* (cat and dog fleas), *Xenopsylla cheopis, Pulex irrattans, Ceratophyllus gallinae, Dermatophilus penetrans*, blood-sucking lice (Anoplura) such as *Linognathus* spp, *Haematopinus* spp, *Solenopotes* spp, *Pediculus humanis*; but also chewing lice (*Mallophaga*) such as *Bovicola (Damalinia) ovis, Bovicola (Damalinia) bovis* and other *Bovicola* spp. Ectoparasites also include members of the order Acarina, such as mites (e.g. *Chorioptes bovis, Cheyletiella* spp., *Dermanyssus gallinae, Ortnithonyssus* spp., *Demodex canis, Sarcoptes scabiei, Psoroptes avis* and *Psorergates* spp. and ticks. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest vertebrates, for example warm-blooded animals including farm animals, such as cattle, horses, pigs, sheep and goats, poultry such as chickens, turkeys, guineafowis and geese, fur-bearing animals such as mink, foxes, chinchillas, rabbits and the like, as well as companion animals such as ferrets, guinea pigs, rats, hamster, cats and dogs, but also humans and fishes.

The compounds of the formula (I) according to the invention are also active against all or individual development stages of animal pests showing normal sensitivity, as well as those showing resistance to widely used parasiticides. This is especially true for resistant insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%. Compounds of the formula (I) can also be used against hygiene pests, especially of the order Diptera of the families Muscidae, Sarcophagidae, Anophilidae and Culicidae; the orders Orthoptera, Dietyoptera (e.g. the family Blattidae (cockroaches), such as *Blatella gerrnanica, Blatta orientalis, Periplaneta americana*) and Hymenoptera (e.g. the families Formicidae (ants) and Vespidae (wasps).

Surprisingly, the compounds of formula (I) are also effective against ectoparasites of fishes, especially the sub-class of Copepoda (e.g. order of Siphonostornatokla (sea lice), whilst being well tolerated by fish.

The compounds of formula (I) can also be used against hygiene pests, especially of the order Diptera of the families Sarcophagidae, Anophilidae and Culicidae; the orders *Orthoptera, Diciyoptera* (e.g. the family Blattidae) and Hymenoptera (e.g. the family Formicidae).

Compounds of the formula (I) also have sustainable efficacy on parasitic mites and insects of plants. In the case of spider mites of the order Acarina, they are effective against eggs, nymphs and adults of Tetranychidae (*Tetranychus* spp. and *Penonychus* spp.).

They have high activity against sucking insects of the order Homoptera, especially against pests of the families Aphididae, Delphacidae, Clcadallidae, Psyllidae, Loccidae, Diaspididae and Eriophydidae (e.g. rust mite on citrus fruits); the orders Hemiptera, Heteroptera and Thysanoptera, and on the plant-eating insects of the orders Lepidoptera, Coleoptera, Diptera and Orthoptera They are similarly suitable as a soil insecticide against pests in the soil.

The compounds of formula (I) are therefore effective against all stages of development of sucking insects and eating insects on crops such as cereals, cotton, rice, maize, soya, potatoes, vegetables, fruit, tobacco, hops, citrus, avocados and other crops.

The compounds of formula I are also effective against plant nematodes of the species *Meloidogyne, Heterodera, Pratylenchus, Ditytenches, Radopholus, Rizoglyphus* etc.

Certain compounds of the formula (I) seem to be also effective against certain species of helminths. Helminths are commercially important because they cause serious diseases in mammals and poultry, e.g. in sheep, pigs, goats, cattle, horses, donkeys, camels, dogs, cats, rabbits, guinea-pigs, hamsters, chicken, turkeys, guinea fowls and other farmed birds, as well as exotic birds. Typical nematodes are: *Haemonchus, Trichostrongylus, Ostertagia, Nematodirus, Cooperia, Ascaris, Bunostonum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris, Parascaris* and *Dirofilaria*. The trematodes include, in particular, the family of Fasciolideae, especially Fasciola hepatica.

The good pesticidal activity of the compounds of formula (I) according to the invention corresponds to a mortality rate of at least 50-60% of the pests mentioned, more preferably to a mortality rate over 90%, most preferably to 95-100%. The compounds of formula (I) are preferably employed internally and externally in unmodified form or preferably together with the adjuvants conventionally used in the art of formulation and may therefore be processed in a known manner to give, for example, liquid formulations (e.g. spot-on, pour-on, spray-on, emulsions, suspensions, solutions, emulsifiable concentrates, solution concentrates), semi-solid formulations (e.g. creams, ointments, pastes, gels, liposomal preparations) and solid preparations (e.g. food additives tablets including e.g. capsules, powders including soluble powders, granules, or embeddings of the active ingredient in polymeric substances, like implants and microparticles). As with the compositions, the methods of application are selected in accordance with the intended objectives and the prevailing circumstances.

The formulation, i.e. preparations containing the active ingredient of formula (I), or combinations of these active ingredients with other active ingredients, and optionally a solid, semi-solid or liquid adjuvant, are produced in a manner known per se, for example by intimately mixing, kneading or dispersing the active ingredients with compositions of excipients, whereby the physiological compatibility of the formulation excipients must be taken into consideration.

The solvents in question may be: alcohols (aliphatic and aromatic), such as benzylalcohol, ethanol, propanol, isopropanol or butanol, fatty alcohols, such as oleyl alcohol and glycols and their ethers and esters, such as glycerin, propylene glycol, dipropylene glycol ether, ethylene glycol, ethylene glycol monomethyl or -ethyl ether and butyl dioxytol, carbonates, such as propylene carbonate, ketones, such as cyclohexanone, isophorone or diacetanol alcohol and polyethylene glycols, such as PEG 300. In addition, the compositions may comprise strong polar solvents, such as N-methyl-2-pyrrolidone, dimethyl sulfoxide or dimethylformamide, or water, fatty acid esters, such as ethyl oleate or isopropylpaimitate, vegetable oils, such as rape, castor, coconut, or soybean oil, synthetic mono-, di-, triglycerides like e.g. glyceryl monostearate and medium chain triglycerides and also, if appropriate, silicone oils. The mentioned ingredients may also serve as carrier for particulate application froms.

As ointment base resp. structure building ingredients the following excipients may be used: Petroleum based substances, such as Vaseline or paraffines, bases made from wool fat, like e.g. lanolin or lanolin alcohols, polyethylene glycols like e.g. macrogols and lipid bases like e.g. phospholipids or triglycerids, such as hydrogenated vegetable oils.

The use of emulsifiers, wetting agents and spreading agents may also be required, in general, lecithins like soy lecithin, salts of fatty acids with alkaline earth and alkali metals, alkyl sulfates like sodium cetylstearyl sulphate, cholates, fatty alcohols like cetyl alcohol, sterols like cholestesterol, polyoxyethylene sorbitan fatty acid esters like polysorbate 20, sorbitan fatty acid esters like sorbitan mono laureate, fatty acid esters and fatty alcohol ethers of polyoxyethylene like poloxyl oleyl ether, polyoxypropylene polyoxyethylene block copolymers as e.g. Pluronic™, saccharose esters like saccharose distearate, polyglyceryl fatty acid esters like polyglycerol oleate and fatty acid esters like e.g. ethyl oleate or isopropylmyristate.

The formulations may also include gelifying and stiffening agents, like e.g. polyacrylic acid derivatives, cellulose ethers, polyvinyl alcohols, polyvinylpyrrolidons and fine disperse silicium dioxide.

As polymeric agents with controlled release properties, may be applied derivatives made by polylactic acid, polylactic coglycolic acid, poly orthoester, polyethylene carbonate, poly anhydrids and starch and PVC based matrices.

The addition of penetration enhancers like ketones, sulfoxides, amides, fatty acid esters and fatty alcohols may be necessary.

Also preservatives like sorbic acid, benzyl alcohol and parabenes, and antioxidants as e.g. alpha tocopherol may be added.

The active ingredient or combinations of the active ingredient may also applied in capsules, like hard gelatine capsules or soft capsules.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), lubricants (e.g. magnesium stearate), glidants (e.g. colloidal silicon dioxide) and disintegrants (e.g. cellulose derivatives) and acid resistant coatings, like e.g. acrylic acid esters.

The compounds of formula (I) according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. For example, in case of a compound of formula (I) having a particular efficacy as adulticide, i.e. since it is effective in particular against the adult stage of the target parasites, the addition of a pesticide which instead attack the juvenile stages of the parasites may be very advantageous, or vice versa. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula (I). Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers. Non-limitative examples of suitable insecticides and acaricides are mentioned in WO 2009/071500, compounds Nos. 1-284 on pages 18-21. Non-limitative examples of suitable anthelminthics are mentioned in WO 2009/071500, compounds (A1)-(A31) on page 21. Non-limitative examples of suitable repellents and detachers are mentioned in WO 2009/071500, compounds (R1)-(R3) on page 21 and 22. Non-limitative examples of suitable synergists are mentioned in WO 2009/071500, compounds (Si)-(53) on page 22. The said partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature.

As a consequence of the above details, a further aspect of the present invention relates to a combination preparation for the control of parasites on vertebrates, in particular on warm-blooded animals or on fishes, characterised in that it contains, in addition to a compound of formula (I), at least one further active ingredient having the same or different sphere of activity and at least one physiologically acceptable carrier. The present invention is not restricted to two-fold combinations.

As a rule, the insecticidal and acaricidal compositions according to the invention contain 0.1 to 99% by weight, especially 0.1 to 95% by weight of one or more active ingredients of formula (I), 99.9 to 1% by weight, especially 99.8 to 5% by weight of a solid or liquid admixture, including 0 to 25% by weight, especially 0.1 to 25% by weight of a surfactant.

Application of the compositions according to the invention to the animals to be treated may take place topically, per-orally, parenterally or subcutaneously, the composition being present, for example, in the form of solutions, emulsions, suspensions, (drenches), powders, tablets, boll, capsules, chewable treats, collars, eartags and pour-on formulations. Preferred topical formulations are understood to refer to a ready-to-use solution in form of a spot-on, pour-on or spray-on formulation often consisting of a dispersion or suspoemulsion or a combination of active ingredient and spreading auxiliaries. The expression spot-on or pour-on method is understood to refer to a ready-to-use concentrate intended to be applied topically and locally on the animal. This sort of formulation is intended to be applied directly to a relatively small area of the animal, preferably on the animal's back and breech or at one or several points along the line of the back and breech. It is applied as a low volume of about 0.05 to 1 ml per kg, preferably about 0.1 ml per kg, with a total volume from 0.1 to 100 ml per animal, preferably limited to a maximum of about 50 ml. However, it goes without saying that the total volume has to be adapted to the animal that is in need of the treatment and will clearly be different, for example, in young cats and in cattle. These pour-on and spot-on formulations are designed to spread all around the animal giving protection or treatment to almost any part of the animal. Even so the administration is carried out by applying a swab or spray of the pour-on or spot-on formulation to a relatively small area of the coat, one observes that from the active substance is dispersed almost automatically over wide areas of the fur owing to the spreading nature of the components in the formulation and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, cook acid esters of saturated fat alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

A pour-on or spot-on formulation generally contains 1 to 98.9% by weight of a compound of formula (I), 0.1 to 80% by weight of dispersing agent and 1 to 98.9% by weight of solvent. The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

Whereas it is preferred to formulate commercial products as concentrates, the end user will often use dilute formulations. However, this depends on the mode of administration. Orally administered products are most often used in diluted form or as feed additives, whereas commercial pour-on and spot-on formulations are normally ready-to-use concentrates. Such compositions may also contain further additives, such as stabilisers, anti-foaming agents, viscosity regulators, binding agents or tackifiers, as well as other active ingredients, in order to achieve special effects.

Insecticidal and acaricidal compositions of this type, which are used by the end user, similarly for a constituent of the present invention.

In each of the processes according to the invention for pest control or in each of the pest control compositions according to the invention, the active ingredients of formula (I) can be used in all of their steric configurations or in mixtures thereof.

The invention also includes a method of prophylactically protecting animals, especially productive livestock, domestic animals and pets, against parasitic helminths, which is characterised in that the active ingredients of formula (I) or the active ingredient formulations prepared therefrom are administered to the animals as an additive to the feed, or to the drinks or also in solid or liquid form, orally or by injection or parenterally. The invention also includes the compounds of formula (I) according to the invention for usage in one of the said processes.

The following examples serve merely to illustrate the invention without restricting it, the term active ingredient representing any substance as described in the preparation examples.

In particular, preferred formulations are made up as follows:

| Formulation examples | | | |
|---|---|---|---|
| 1. Granulate | | a) | b) |
| (i) | active ingredient | 5% | 10% |
| | kaolin | 94% | — |
| | highly dispersed silicic acid | 1% | — |
| | attapulgite | — | 90% |

(% = percent by weight)

The active ingredient is dissolved in methylene chloride, sprayed onto the carrier and the solvent subsequently concentrated by evaporation under vacuum. Granulates of this kind can be mixed with the animal feed.

| (ii) | active ingredient | 3% |
|---|---|---|
| | polyethylene glycol (mw 200) | 3% |
| | kaolin | 94% |

(mw = molecular weight)

The finely ground active ingredient is evenly applied in a mixer to the kaolin which has been moistened with polyethylene glycol. In this way, dust-free coated granules are obtained.

| 2. Tablets or boli | | |
|---|---|---|
| I | active ingredient | 33.00% |
| | methylcellulose | 0.80% |
| | silicic acid, highly dispersed | 0.80% |
| | corn starch | 8.40% |
| II | lactose, cryst. | 22.50% |
| | corn starch | 17.00% |
| | microcryst. cellulose | 16.50% |
| | magnesium stearate | 1.00% |

I Methyl cellulose is stirred into water. After the material has swollen, silicic acid is stirred in and the mixture homogeneously suspended. The active ingredient and the corn starch are mixed. The aqueous suspension is worked into this mixture and kneaded to a dough. The resulting mass is granulated through a 12 M sieve and dried.
II All 4 excipients are mixed thoroughly.
III The preliminary mixes obtained according to I and II are mixed and pressed into tablets or boli.

| 3. injectables | | |
|---|---|---|
| A. Oily vehicle (slow release) | | |
| (i) | active ingredient | 0.1-1.0 g |
| | groundnut oil | ad 100 ml |
| (ii) | active ingredient | 0.1-1.0 g |
| | sesame oil | ad 100 ml |

Preparation: The active ingredient is dissolved in part of the oil whilst stirring and, if required, with gentle heating, then after cooling made up to the desired volume and sterile-filtered through a suitable membrane filter with a pore size of 0.22 μm.

| B. Water-miscible solvent (average rate of release) | | |
|---|---|---|
| (i) | active ingredient | 0.1-1.0 g |
| | 4-hydroxymethyl-1,3-dioxolane (glycerol formal) | 40 g |
| | 1,2-propanediol | ad 100 ml |
| (ii) | active ingredient | 0.1-1.0 g |
| | glycerol dimethyl ketal | 40 g |
| | 1,2-propanediol | ad 100 ml |

Preparation: The active ingredient is dissolved in part of the solvent whilst stirring, made up to the desired volume and sterile-filtered through a suitable membrane filter with a pore size of 0.22 μm.

| C. Aqueous solubilisate (rapid release) | | |
|---|---|---|
| (i) | active ingredient | 0.1-1.0 g |
| | polyethoxylated castor oil (40 ethylene oxide units) | 10 g |
| | 1,2-propanediol | 20 g |
| | benzyl alcohol | 1 g |
| | aqua ad inject. | ad 100 ml |
| (ii) | active ingredient | 0.1-1.0 g |
| | polyethoxylated sorbitan monooleate (20 ethylene oxide units) | 8 g |
| | 4-hydroxymethyl-1,3-dioxolane (glycerol formal) | 20 g |
| | benzyl alcohol | 1 g |
| | aqua ad inject. | ad 100 ml |

Preparation: The active ingredient is dissolved in the solvents and the surfactant, and made up with water to the desired volume. Sterile filtration through an appropriate membrane filter of 0.22 μm pore size.

| 4. Pour on | | |
|---|---|---|
| (i) | active ingredient | 5 g |
| | isopropyl myristate | 10 g |
| | isopropanol | ad 100 ml |
| (ii) | active ingredient | 2 g |
| | hexyl laurate | 5 g |
| | medium-chained triglyceride | 15 g |
| | ethanol | ad 100 ml |
| (iii) | active ingredient | 2 g |
| | oleyl oleate | 5 g |
| | N-methyl-pyrrolidone | 40 g |
| | isopropanol | ad 100 ml |

| 5. Spot on | | |
|---|---|---|
| (i) | active ingredient | 0-15 g |
| | diethyleneglycol monoethylether | ad 100 ml |
| (ii) | active ingredient | 10-15 g |
| | octyl palmitate | 10 g |
| | isopropanol | ad 100 ml |
| (iii) | active ingredient | 10-15 g |
| | isopropanol | 20 g |
| | benzyl alcohol | ad 100 ml |

| 6. Spray on | | |
|---|---|---|
| (i) | active ingredient | 1 g |
| | isopropanol | 40 g |
| | propylene carbonate | ad 100 ml |
| (ii) | active ingredient | 1 g |
| | propylene glycol | 10 g |
| | isopropanol | ad 100 ml |

The aqueous systems may also preferably be used for oral and/or intraruminal application. The compositions may also contain further additives, such as stabilisers, e.g. where appropriate epoxidised vegetable oils (epoxidised coconut oil, rapeseed oil, or soybean oil); antifoams, e.g. silicone oil, preservatives, viscosity regulators, binders, tackifiers, as well as fertilisers or other active ingredients to achieve special effects.

Further biologically active substances or additives, which are neutral towards the compounds of formula (I) and do not have a harmful effect on the host animal to be treated, as well as mineral salts or vitamins, may also be added to the described compositions.

The following examples serve to illustrate the invention. The letter 'h' stands for hour. The starting materials are known and partially commercially available or may be produced in analogy to methods known per se.

Analysis of the purified samples is in each case done using a Waters Autopurification (HPLC/MS) system with a reversed phase column using either method A or B described below. The samples are characterized by rat and retention time. The above-given retention times relate in each case to the use of a solvent system comprising two different solvents, solvent A: $H_2O+0.01\%$ HCOOH, and solvent B: $CH_3CN+0.01\%$ HCOOH).

Method A: column Daisogel SP-120-ODS-AP 5 μm, 150×3 mm) from Bischoff, Leonberg, Germany, flow rate of 2.00 mL/min with a time-dependent gradient as given in the Table:

| Time [min] | A [%] | B [%] |
|---|---|---|
| 0.5 | 90 | 10 |
| 1.0 | 74 | 26 |
| 1.5 | 60 | 40 |
| 2.0 | 47 | 53 |
| 2.5 | 36 | 64 |
| 3.0 | 26 | 74 |
| 3.5 | 19 | 81 |
| 4.0 | 13 | 87 |
| 4.25 | 10 | 90 |
| 4.5 | 8 | 92 |
| 4.75 | 7 | 93 |
| 5.0 | 6 | 94 |
| 5.5 | 5 | 95 |
| 6.5 | 5 | 95 |

Method B: column Waters XTerra MS C18 5 μm, 50×4.6 mm (Waters), flow rate of 3.00 mL/min with a time-dependent gradient as given in the Table:

| Time [min] | A [%] | B [%] |
|---|---|---|
| 0 | 90 | 10 |
| 0.5 | 90 | 10 |
| 2.5 | 5 | 95 |
| 2.8 | 5 | 95 |
| 2.9 | 90 | 10 |
| 3.0 | 90 | 10 |

EXAMPLE 1

Preparation of N-{5-[5-(3,5-dichloro-phenyl)-5-trifluoromethyl-4,5-dihydro-isoxazol-3-yl]-2-methyl-thiophen-3-ylmethyl}-propionamide (compound 1.6 in Table 1)

Step A:

Bromine (9.7 ml) is added to a solution of 2-acetyl-5-methylthiophene (26.6 g) and NaOAc (17.2 g) in water (100 ml) at room temperature. After 12 hours at room temperature the reaction is quenched with a 1M aqueous solution of sodium thiosulfate (100 ml) and extracted three times with ethyl acetate (250 ml). The organic phases are combined, washed with a saturated aqueous solution of NaCl, dried over $MgSO_4$ and concentrated in vacuo to yield 1-(4-bromo-5-methyl-thiophen-2-yl)-ethanone (41.8 g) as a brown oil. The crude product is used without further purification.

Step B:

LiH (3.2 g) is added to a solution of 1-(3,5-dichloro-phenyl)-2,2,2-trifluoro-ethanone (56 g) and 1-(4-bromo-5-methyl-thiophen-2-yl)-ethanone (41 g) in dry THF (500 ml). After 5 h at 60° C. under nitrogen atmosphere, tert-butylmethylether (500 ml) is added to the reaction mixture. The reaction is slowly quenched with water (500 ml) at 5° C. and further extracted twice with tert-butylmethylether (500 ml). The organic phases are combined, washed with a saturated aqueous solution of NaCl, dried over $MgSO_4$ and concentrated in vacuo to yield 1-(4-bromo-5-methyl-thiophen-2-yl)-3-(3,5-dichloro-phenyl)-4,4,4-trifluoro-3-hydroxy-butan-1-one (110 g, 77% purity) as a brown oil. The crude product is used without further purification.

Step C:

Triethylamine (53 ml) and trifluoracetic anhydride (38 ml) are added to a solution of -(4-bromo-5-methyl-thiophen-2-yl)-3-(3,5-dichloro-phenyl)-4,4,4-trifluoro-3-hydroxy-butan-1-one (110 g, 77% purity) at 0° C. After 12 hours at room temperature, the reaction is quenched with water (200 ml) and a saturated aqueous solution of $NaHCO_3$. The aqueous phase is separated and further extracted with two times dichloromethane. The organic phases are combined, washed with water, dried over $MgSO_4$ and concentrated in vacuo to yield 1-(4-bromo-5-methyl-thiophen-2-yl)-3-(3,5-dichloro-phenyl)-4,4,4-trifluoro-but-2-en-1-one (95 g, 71% purity) as a brown oil. The crude product is used without further purification.

Step D:

Hydroxylamine hydrochloride (13 g) and NaOH (18 g) are added to a solution of 1-(4-bromo-5-methyl-thiophen-2-yl)-3-(3,5-dichloro-phenyl)-4,4,4-trifluoro-but-2-en-1-one (84 g, 71% purity) in EtOH (1000 ml) at room temperature. After 12 hours at room, the reaction mixture is concentrated in vacuo, diluted with diethylether and water. The aqueous phase is separated and further extracted two times with diethylether. The organic phases are combined, washed with a saturated aqueous solution of NaCl, dried over $MgSO_4$ and concentrated in vacuo. The crude product is purified by chromatography on silica gel (1800 g) eluting with a mixture of heptane and dichloromethane (4:1) to yield 3-(4-bromo-5-methyl-thiophen-2-yl)-5-(3,5-dichloro-phenyl)-5-trifluoromethyl-4,5-dihydro-isoxazole (47 g) as a light brown crystals.

Step E:

Tetrakis(triphenylphosphine)palladium(0) (1.2 g) is added to a solution of $Zn(CN)_2$ (1.2 g) and 3-(4-bromo-5-methyl-thiophen-2-yl)-5-(3,5-dichloro-phenyl)-5-trifluoromethyl-4,5-dihydro-isoxazole (4.6 g) in DMF (12 ml). After 1 h at 120° C. in the microwave, the reaction is quenched with water (150 ml) and ethyl acetate (100 ml) and filtered over celite. The aqueous phase is separated and further extracted two times with ethyl acetate. The organic phases are combined, washed with a saturated aqueous solution of NaCl, dried over $MgSO_4$ and concentrated in vacuo. The crude product is purified on a semi-preparative HPLC to yield 5-[5-(3,5-dichloro-phenyl)-5-trifluoromethyl-4,5-dihydro-isoxazol-3-yl]-2-methyl-thiophene-3-carbonitrile (2.2 g) as a beige crystal.

Step F:

Borane dimethyl sulfide complex (0.73 ml) is added to a solution of 5-[5-(3,5-dichloro-phenyl)-5-trifluoromethyl-4,5-dihydro-isoxazol-3-yl]-2-methyl-thiophene-3-carbonitrile (2.8 g) in THF (21 ml) at reflux. After 30 minutes at reflux, the reaction is cooled down to room temperature. HCl (6.2 ml, 1.25M in MeOH) is added and the reaction mixture is refluxed for 30 minutes. The mixture is then concentrated in vacuo to yield C-{5-[5-(3,5-dichloro-phenyl)-5-trifluoromethyl-4,5-dihydro-isoxazol-3-yl]-2-methyl-thiophen-3-yl}-methylamine as a brown foam (2.9 g). The crude product is used without further purification.

Step G:

Propionyl chloride (0.17 ml) is added to a solution of C-{5-[5-(3,5-dichloro-phenyl)-5-trifluoromethyl-4,5-dihydro-isoxazol-3-yl]-2-methyl-thiophen-3-yl}-methylamine (816 mg) and DIPEA (1 ml) in dichloromethane (10 ml) at room temperature. After 3 hours at RT, the reaction is quenched with water. The aqueous phase is separated and further extracted two times with dichloromethane. The organic phases are combined, dried over MgSO$_4$ and concentrated in vacuo. The crude product is purified on a semi-preparative HPLC and by crystallization in a diethylether/petroleum ether mixture to yield N-{5-[5-(3,5-dichloro-phenyl)-5-trifluoromethyl-4,5-dihydro-isoxazol-3-yl]-2-methyl-thiophen-3-ylmethyl}-propionamide (compound 1.6, 122 mg) as white crystals. MS (HPLC/MS): 465 (MH$^+$). Retention time: 1.96 min.

EXAMPLE 2

Preparation of 3-cyano-N-{5-[5-(3,5-dichloro-phenyl)-5-trifluoromethyl-4,5-dihydro-isoxazol-3-yl]-2-methyl-thiophen-3-ylmethyl}-propionamide (Compound 1.39 in Table 1)

3-Cyanopropionic acid (104 mg) and PyBOP (400 mg) are added to a solution of DIPEA (0.36 ml) and C-{5-[5-(3,5-dichloro-phenyl)-5-trifluoromethyl-4,5-dihydro-isoxazol-3-yl]-2-methyl-thiophen-3-yl}-methylamine (286 mg, Example 1, step F) in dichloromethane (5 ml). After 4 hours at RT, the reaction is quenched with water. The aqueous phase is separated and further extracted two times with dichloromethane. The organic phases are combined, dried over MgSO$_4$ and concentrated in vacuo. The crude product is purified on a semi-preparative HPLC to yield 3-cyano-N-{5-[5-(3,5-dichloro-phenyl)-5-trifluoromethyl-4,5-dihydro-isoxazol-3-yl]-2-methyl-thiophen-3-ylmethyl}-propionamide (compound 1.39, 67 mg) as a beige resin. MS (HPLC/MS): 491 (MH$^+$). Retention time: 1.90 min.

EXAMPLE 3

Preparation of tetrahydro-furan-3-carboxylic acid {2-methyl-5-[5-(3,4,5-trichloro-phenyl)-5-trifluoromethyl-4,5-dihydro-isoxazol-3-yl]-furan-3-ylmethyl}-amide (Compound 2.3 in Table 2)

Step A:

Phosphorus oxychloride (33 ml) is added dropwise to a solution of 2-methyl-furan-3-carboxylic acid methyl ester (25.0 g) in DMF (75 ml) under nitrogen at 0° C. After 3 h 30 at 40° C., the reaction mixture is slowly poured onto water at 0° C. and NaOH 5 N is added carefully. The mixture is extracted three times with diethyl ether. The combined organic phases are washed with a saturated aqueous solution of NaHCO$_3$, dried over Na$_2$SO$_4$ and concentrated in vacuo.

The crude product is purified by chromatography on silica gel eluting with a mixture of diethyl ether and ethyl acetate (3:1) to yield 5-formyl-2-methyl-furan-3-carboxylic acid methyl ester (22.36 g) as a yellow solid. MS (HPLC/MS): 169 (MH$^+$).

Step B:

Methylmagnesium bromide (370.5 ml, 1.4M in THF) is added over 30 minutes to a solution of 5-formyl-2-methyl-furan-3-carboxylic acid methyl ester (87.2 g) in THF (1200 ml) under nitrogen at 0° C. After 1 hour at 0° C., the reaction is quenched with a saturated aqueous solution of NH$_4$Cl in water. The mixture is stirred 1 hour at 0° C. and then is extracted three times with ethyl acetate. The organic phases are combined, dried over Na$_2$SO$_4$ and concentrated in verve to yield 5-(1-hydroxy-ethyl)-2-methyl-furan-3-carboxylic acid methyl ester (94.5 g) as a yellow solid. The crude product obtained is used without further purification. MS (HPLC/MS): 185 (MH$^+$).

Step C:

Manganese dioxide (669 g) is added portionwise to a solution of 5-(1-hydroxy-ethyl)-2-methyl-furan-3-carboxylic acid methyl ester (94.5 g) in dichloromethane (1000 ml). After 72 hours at room temperature, the reaction mixture is filtered through a plug of silica gel and the filtration cake is washed several times with ethyl acetate. The filtrate is concentrated in verve to yield 5-acetyl-2-methyl-furan-3-carboxylic acid methyl ester (78 g) as a yellow solid. The crude product obtained is used without further purification. MS (HPLC/MS): 183 (MH$^+$).

Step D:

n-BuLi (16.5 ml, 2.5M in hexane) is added over 20 minutes to a solution of 5-bromo-1,2,6-trichloro-benzene (10.2 g) in diethyl ether (150 ml) under nitrogen at −78° C. After 20 minutes at −78° C., a solution of ethyl trifluoroacetate (5.15 ml) in diethyl ether (50 ml) is added over 15 minutes to the reaction mixture. After 40 minutes at −78° C., the reaction mixture is slowly warmed up to room temperature and then quenched with a saturated aqueous solution of NH$_4$Cl. The aqueous phase is extracted three times with diethyl ether. The combined organic phases are dried over Na$_2$SO$_4$ and concentrated in vacuo. The crude product is purified by vacuum distillation to yield 2,2,2-trifluoro-1-(3,4,5-trichloro-phenyl)-ethanone (9.20 g) as a yellow solid.

Step E:

LiH (1.76 g) is added to a solution of 2,2,2-trifluoro-1-(3,4,5-trichloro-phenyl)-ethanone (35.33 g) and 5-acetyl-2-methyl-furan-3-carboxylic acid methyl ester (20 g) in THF (300 ml). After 1 hour 30 at 60° C. MTBE is added (450 ml) and the reaction mixture is poured onto water (750 ml) at 0° C. The organic phase is washed with water and a saturated aqueous solution of NaCl dried over MgSO$_4$ and concentrated in vacuo to yield 62.3 g of 2-methyl-5-[4,4,4-trifluoro-3-hydroxy-3-(3,4,5-trichloro-phenyl)-butyryl]-furan-3-carboxylic acid methyl ester. The crude product is used without further purification. MS (HPLC/MS): 459 (MH$^+$).

Step F:

Trifluoroacetic anhydride (21.5 ml) is added dropwise to a solution of 2-methyl-5-[4,4,4-trifluoro-3-hydroxy-3-(3,4,5-trichloro-phenyl)-butyryl]-furan-3-carboxylic acid methyl ester (50.5 g) and triethylamine (30.6 ml) in dichloromethane (700 ml). After 30 minutes at room temperature, the reaction is diluted with water and the aqueous phase is extracted two times with dichloromethane. The combined organic phases are washed once with a saturated solution of NaHCO$_3$, with water and with a saturated aqueous solution of NaCl, dried over Na$_2$SO$_4$ and concentrated in vacuo. The crude product is purified by chromatography on silica gel eluting with a mixture of heptane and ethyl acetate (95:5) to yield (E/Z)-2-methyl-5-[4,4,4-trifluoro-3-(3,4,5-trichloro-phenyl)-but-2-enoyl]-furan-3-carboxylic acid methyl ester (29.1 g) as a yellow solid. MS (HPLC/MS): 441 (MH$^+$).

Step G:

Cesium hydroxyde monohydrate (33.2 g) and hydroxylamine hydrochloride (9.16 g) are added to a solution of (E/Z)-2-methyl-5-[4,4,4-trifluoro-3-(3,4,5-trichloro-phenyl)-but-2-enoyl]-furan-3-carboxylic acid methyl ester (29.1 g) in dichloromethane (650 ml) at 0° C. The mixture is slowly warmed up to room temperature and stirred during 1 hour 30. The reaction mixture is quenched with water. The organic phase is separated and washed two times with HCl 2M, dried over Na$_2$SO$_4$ and concentrated in vacuo. The crude product is purified by chromatography on silica gel (1400 g) eluting with a mixture of heptane and ethyl acetate (95:5 to 90:10) to yield 2-methyl-5-[5-(3,4,5-trichloro-phenyl)-5-trifluoromethyl-4,5-dihydro-isoxazol-3-yl]-furan-3-carboxylic acid methyl ester (8.69 g) as a white solid. MS (HPLC/MS): 456 (MH$^+$).

Step H:

Diisobutylaluminium hydride (DIBAL-H, 21.9 ml, 1M in toluene) is added to a solution of 2-methyl-5-[5-(3,4,5-trichloro-phenyl)-5-trifluoromethyl-4,5-dihydro-isoxazol-3-yl]-furan-3-carboxylic acid methyl ester (5.0 g) in diethyl ether (100 ml) under nitrogen at −5° C. After 15 it at −5° C., the cold bad is removed. After 20 hours at room temperature, the reaction mixture is diluted with ethyl acetate and is quenched with a saturated solution of NaHCO$_3$. The organic phase is separated and washed with a saturated solution of NaHCO$_3$ and with a saturated aqueous solution of NaCl, dried over Na$_2$SO$_4$ and concentrated in vacuo. The crude product is purified on a semi-preparative HPLC to yield {2-methyl-5-[5-(3,4,5-trichloro-phenyl)-5-trifluoromethyl-4,5-dihydro-isoxazol-3-yl]-furan-3-yl}-methanol (3.88 g) as a white foam. MS (HPLC/MS): 428 (MH$^+$).

Step I:

Manganese dioxide (9.64 g) is added portion-wise to a solution of {2-methyl-5-[5-(3,4,5-trichloro-phenyl)-5-trifluoromethyl-4,5-dihydro-isoxazol-3-yl]-furan-3-yl}-methanol (3.88 g) in dichloromethane (100 ml). After 18 hours at room temperature, the reaction mixture is filtered through a plug of celite and the filtration cake is washed with dichloromethane. The filtrate is concentrated in vacuo to yield 2-methyl-5-[5-(3,4,5-trichloro-phenyl)-5-trifluoromethyl-4,5-dihydro-isoxazol-3-yl]-furan-3-carbaldehyde (3.16 g) as a white foam. The crude product obtained is used without further purification. MS (HPLC/MS): 426 (MH$^+$).

Step J:

A mixture of 2-methyl-5-[5-(3,4,5-trichloro-phenyl)-5-trifluoromethyl-4,5-dihydro-isoxazol-3-yl]-furan-3-carbaldehyde (2.15 g), tert-butylcarbamate (1.80 g), trifluoroacetic acid (0.78 ml) and triethylsilane (2.48 ml) in acetonitrile (23 ml) is stirred at room temperature for 20 hours. After diluting with ethyl acetate, the reaction mixture is quenched with a saturated solution of NaHCO$_3$. The organic phase is separated and the aqueous phase is extracted once with ethyl acetate. The combined organic phases are washed with a saturated solution of NaHCO$_3$ and with a saturated aqueous solution of NaCl, dried over MgSO$_4$ and concentrated in vacuo. The crude product is purified on a semi-preparative HPLC to yield {2-methyl-5-[5-(3,4,5-trichloro-phenyl)-5-trifluoromethyl-4,5-dihydro-isoxazol-3-yl]-furan-3-ylmethyl}-carbamic acid tert-butyl ester (2.10 g, compound 2.4 in Table 2) as a light yellow foam. MS (HPLC/MS): 527 (MH$^+$).

Step K:

Trifluoroacetic acid (6.0 ml) is added to a solution of {2-methyl-5-[5-(3,4,5-trichloro-phenyl)-5-trifluoromethyl-4,5-dihydro-isoxazol-3-yl]-furan-3-ylmethyl}-carbamic acid tert-butyl ester (2.05 g) in dichloromethane (20 ml). After 45 min at room temperature, an aqueous solution of NaOH (2M) is added until pH 12 is reached and the reaction mixture is extracted three times with dichloromethane. The combined organic phases are washed with a saturated solution of NaCl, dried over Na$_2$SO$_4$ and concentrated in vacuo to yield C-{2-methyl-5-[5-(3,4,5-trichloro-phenyl)-5-trifluoromethyl-4,5-dihydro-isoxazol-3-yl]-furan-3-yl}-methylamine (1.64 g, compound 2.5 in Table 2) as a light yellow foam. The crude product obtained is used without further purification. MS (HPLC/MS): 410 (MH), Retention time: 1.27 min.

Step L:

Tetrahydro-furan-3-carboxylic acid (81 mg), PyBOP (268 mg) and DIPEA (0.244 ml) are added to a solution of C-{2-methyl-5-[5-(3,4,5-trichloro-phenyl)-5-trifluoromethyl-4,5-dihydro-isoxazol-3-yl]-furan-3-yl}-methylamine (200 mg) in dichloromethane (4 ml). After 24 hours at room temperature, the reaction is quenched with water. The reaction mixture is extracted three times with dichloromethane. The combined organic phases are washed with a saturated solution of NaHCO$_3$ and with a saturated aqueous solution of NaCl, dried over Na$_2$SO$_4$ and concentrated in vacuo. The crude product is purified on a semi-preparative HPLC to yield tetrahydro-furan-3-carboxylic acid {2-methyl-5-[5-(3,4,5-trichloro-phenyl)-5-trifluoromethyl-4,5-dihydro-isoxazol-3-yl]-furan-3-ylmethyl}-amide (189 mg, compound 2.3 in Table 2) as a white foam. MS (HPLC/MS): 525 (MH$^+$). Retention time: 1.97 min.

EXAMPLE 4

Preparation of cyclopropanecarboxylic acid {2-methyl-5-[5-(3,4,5-trichloro-phenyl)-5-trifluoromethyl-4,5-dihydro-isoxazol-3-yl]-furan-3-ylmethyl}-amide (Compound 2.2 in Table 2)

A mixture of 2-methyl-5-[5-(3,4,5-trichloro-phenyl)-5-trifluoromethyl-4,5-dihydro-isoxazol-3-yl]-furan-3-carbaldehyde (250 mg, Example 3, step I), cyclopropanecarboxylic acid amide (160 mg), trifluoroacetic acid (0.142 ml) and triethylsilane (0.301 ml) in toluene (4 ml) is refluxed overnight. After 23 hours the reaction mixture is concentrated in vacuo. The crude product is purified on a semi-preparative HPLC to yield cyclopropanecarboxylic acid {2-methyl-5-[5-(3,4,5-trichloro-phenyl)-5-trifluoromethyl-4,5-dihydro-isoxazol-3-yl]-furan-3-ylmethyl}-amide (251 mg, compound 2.2 in Table 2) as a yellowish foam. MS (HPLC/MS): 495 (MH$^+$). Retention time: 2.02 min.

The substances named in the following Table 1 are prepared analogously to the above-described methods. The compounds are of formula

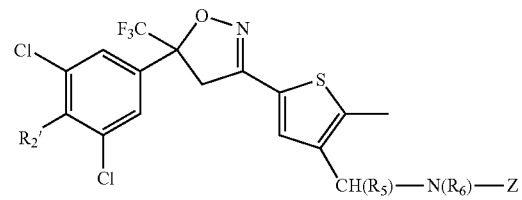

wherein the meaning of the variables is given in Table 1.

The following physical data are obtained according to the above-described HPLC/MS characterization process. The values the melting point are indicated in ° C.
TABLE 1
| Compound No. | —CH(R$_5$)—N(R$_6$)—Z | R$_2$' | Analytical Method | EM$_{calcd}$ | m/z | R$_{t*b}$ [min] |
|---|---|---|---|---|---|---|
| 1.1 | 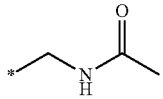 | H | B | 450 | 451 | 1.65 |
| 1.2 | 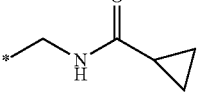 | H | B | 476 | 477 | 2.01 |
| 1.3 | 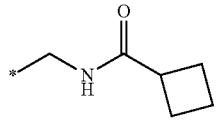 | H | B | 490 | 491 | 2.09 |
| 1.4 | 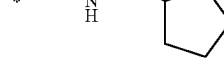 | H | | | | |
| 1.5 | 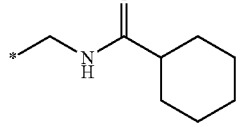 | Cl | A | 552 | 553 | 4.88 |
| 1.6 | 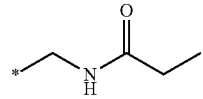 | H | B | 464 | 465 | 1.96 |
| 1.7 | 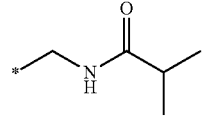 | H | | | | |
| 1.8 | 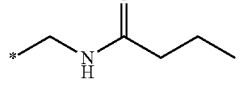 | H | B | 478 | 479 | 2.05 |
| 1.9 | 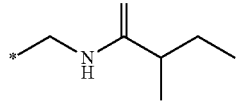 | H | | | | |
| 1.10 | 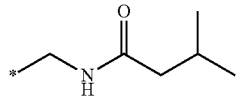 | H | | | | |
| 1.11 | 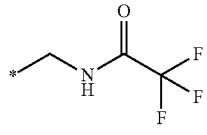 | H | | | | |

TABLE 1-continued

| Compound No. | —CH(R₅)—N(R₆)—Z | R₂' | Analytical Method | EM$_{calcd}$ | m/z | R$_{t}$*$^{b}$ [min] |
|---|---|---|---|---|---|---|
| 1.12 | *-CH₂-NH-C(O)-CH₂-CF₃ | H | B | 518 | 519 | 2.06 |
| 1.13 | *-CH₂-NH-C(O)-CF₂-CF₃ | H | | | | |
| 1.14 | *-CH₂-NH-C(O)-CF₂-CF₂-CF₃ | H | | | | |
| 1.15 | *-CH₂-NH-C(O)-O-C(CH₃)₃ | H | | | | |
| 1.16 | *-CH₂-NH₂ | H | B | 408 | 407 | 1.3 |
| 1.17 | *-CH₂-NH-C(O)-(3-pyridyl) | H | | | | |
| 1.18 | *-CH₂-NH-C(O)-(4-pyridyl) | Cl | A | 547 | 548 | 5.42 |
| 1.19 | *-CH₂-NH-C(O)-(2-pyrimidyl) | H | | | | |
| 1.20 | *-CH₂-NH-C(O)-(4-pyrimidyl) | Cl | A | 548 | 549 | 4.47 |
| 1.21 | *-CH₂-NH-C(O)-phenyl | Cl | A | 546 | 547 | 4.67 |
| 1.22 | *-CH₂-NH-C(O)-(2-Cl-phenyl) | H | | | | |

TABLE 1-continued

| Compound No. | —CH(R₅)—N(R₆)—Z | R₂' | Analytical Method | EM$_{calcd}$ | m/z | R$_t$*$_b$ [min] |
|---|---|---|---|---|---|---|
| 1.23 | *-CH₂-NH-C(O)-(3-Cl-phenyl) | H | | | | |
| 1.24 | *-CH₂-NH-C(O)-(4-Cl-phenyl) | Cl | A | 580 | 581 | 4.98 |
| 1.25 | *-CH₂-NH-C(O)-(2-OMe-phenyl) | H | | | | |
| 1.26 | *-CH₂-NH-C(O)-(3-OMe-phenyl) | Cl | A | 576 | 577 | 4.72 |
| 1.27 | *-CH₂-NH-C(O)-(4-OMe-phenyl) | H | | | | |
| 1.28 | *-CH₂-NH-C(O)-CH₂-OMe | H | B | 480 | 481 | 1.96 |
| 1.29 | *-CH₂-NH-C(O)-CH₂-OEt | H | | | | |
| 1.30 | *-CH₂-NH-C(O)-CH₂CH₂-OMe | Cl | A | 528 | 529 | 4.18 |
| 1.31 | *-CH₂-NH-C(O)-S-Me | H | | | | |
| 1.32 | *-CH₂-NH-C(O)-CH₂-S-Me | H | B | 496 | 497 | 2.02 |
| 1.33 | *-CH₂-NH-C(O)-CH₂-S(O)₂-Me | H | | | | |

TABLE 1-continued

| Compound No. | —CH(R$_5$)—N(R$_6$)—Z | R$_2$' | Analytical Method | EM$_{calcd}$ | m/z | R$_{t\,*b}$ [min] |
|---|---|---|---|---|---|---|
| 1.34 | | H | | | | |
| 1.35 | | H | | | | |
| 1.36 | | H | | | | |
| 1.37 | | Cl | A | 560 | 561 | 3.66 |
| 1.38 | | H | B | 475 | 476 | 1.93 |
| 1.39 | | H | B | 489 | 490 | 1.91 |
| 1.40 | | H | | | | |
| 1.41 | | H | | | | |
| 1.42 | | H | | | | |
| 1.43 | | H | | | | |
| 1.44 | | H | B | 506 | 507 | 1.90 |

TABLE 1-continued

| Compound No. | —CH(R$_5$)—N(R$_6$)—Z | R$_2$' | Analytical Method | EM$_{calcd}$ | m/z | R$_{t}$*$_{b}$ [min] |
|---|---|---|---|---|---|---|
| 1.45 | *—CH$_2$—NH—C(O)—(tetrahydro-2H-pyran-4-yl) | H | | | | |
| 1.46 | *—CH$_2$—NH—C(O)—(tetrahydro-2H-thiopyran-4-yl) | H | | | | |
| 1.47 | *—CH$_2$—NH—C(O)—(thiazol-2-yl) | H | | | | |
| 1.48 | *—CH$_2$—NH—C(O)—(thiophen-2-yl) | H | | | | |
| 1.49 | *—CH$_2$—NH—S(O)$_2$—CH$_3$ | H | | | | |
| 1.50 | *—CH$_2$—NH—S(O)$_2$—CH$_2$CH$_3$ | H | | | | |
| 1.51 | *—CH$_2$—NH—C(O)—C≡C—CH$_3$ | Cl | A | 508 | 509 | 4.39 |
| 1.52 | *—CH$_2$—NH—C(O)—C(O)—CH$_3$ | H | | | | |
| 1.53 | *—CH$_2$—NH—C(O)—CH$_2$—NH—C(O)—CF$_3$ | H | | | | |
| 1.54 | *—CH$_2$—NH—C(O)—CH$_2$—(2-methyl-1,3-dioxolan-2-yl) | H | | | | |
| 1.55 | *—CH$_2$—NH—C(O)—CH$_2$CH$_3$ | Cl | B | 498 | 499 | 2.10 |

TABLE 1-continued

| Compound No. | —CH(R₅)—N(R₆)—Z | R₂' | Analytical Method | EM$_{calcd}$ | m/z | R$_{t}$*$_{b}$ [min] |
|---|---|---|---|---|---|---|
| 1.56 | -cyclopropyl) | Cl | B | 510 | 511 | 2.14 |
| 1.57 | -tetrahydrofuran-3-yl) | Cl | A | 540 | 541 | 4.12 |
| 1.58 | -CH2-CH2-S-CH3) | Cl | A | 544 | 545 | 4.43 |

The substances named in the following Table 2 are prepared analogously to the above-described methods. The compounds are of formula

wherein the meaning of the variables is given in Table 2.

The following physical data are obtained according to the above-described HPLC/MS characterization process. The values of the melting point are indicated in ° C.

TABLE 2

| Compound No. | —CH(R₅)—N(R₆)—Z | R₂' | Analytical method | EMcalcd | m/z | Rt *b [min] |
|---|---|---|---|---|---|---|
| 2.1 | -CH2CH3) | Cl | B | 482 | 483 | 2.00 |
| 2.2 | -cyclopropyl) | Cl | B | 494 | 495 | 2.02 |
| 2.3 | -tetrahydrofuran-3-yl) | Cl | B | 524 | 525 | 1.97 |
| 2.4 | -O-C(CH3)3) | Cl | B | 526 | | |
| 2.5 | *-CH2-NH2 | Cl | B | 426 | 427 | 1.27 |

TABLE 2-continued

| Compound No. | —CH(R₅)—N(R₆)—Z | R₂' | Analytical method | EMcalcd | m/z | Rt *b [min] |
|---|---|---|---|---|---|---|
| 2.6 | *-CH₂-NH-C(O)-CH₂CH₂CH₃ | Cl | B | 496 | 497 | 2.11 |
| 2.7 | *-CH₂-NH-C(O)-cyclobutyl | Cl | B | 508 | 509 | 1.98 |
| 2.8 | *-CH₂-NH-C(O)-CH₃ | Cl | B | 568 | 569 | 1.94 |
| 2.9 | *-CH₂-NH-C(O)-CH₂-S-CH₃ | Cl | B | 514 | 515 | 2.08 |
| 2.10 | *-CH₂-NH-C(O)-CH₂-CN | Cl | B | 493 | 494 | 2.00 |
| 2.11 | *-CH₂-NH-C(O)-CH₂CH₂-CN | Cl | B | 507 | 508 | 1.98 |
| 2.12 | *-CH₂-NH-C(O)-CH₂-O-CH₃ | Cl | B | 498 | 499 | 2.03 |
| 2.13 | *-CH₂-NH-C(O)-CH₂-CF₃ | Cl | B | 536 | 537 | 2.13 |
| 2.14 | *-CH₂-NH-C(O)-CH₂CH₂-O-CH₃ | Cl | B | 512 | 513 | 1.73 |
| 2.15 | *-CH₂-NH-C(O)-CH₂CH₂-S-CH₃ | Cl | B | 528 | 529 | 1.93 |
| 2.16 | *-CH₂-NH-C(O)-CH₂CH₂-S(O)-CH₃ | Cl | B | 544 | 545 | 1.52 |
| 2.17 | *-CH₂-NH-C(O)-CH₂CH₂-S(O)₂-CH₃ | Cl | B | 560 | 561 | 1.65 |
| 2.18 | *-CH(CH₃)-NH-C(O)-CH₂CH₃ | Cl | B | 496 | 497 | 1.93 |

TABLE 2-continued

| Compound No. | —CH(R$_5$)—N(R$_6$)—Z | R$_2$' | Analytical method | EMcalcd | m/z | Rt *b [min] |
|---|---|---|---|---|---|---|
| 2.19 | | Cl | B | 508 | 509 | 1.86 |
| 2.20 | | Cl | | 524 | 525 | |
| 2.21 | | Cl | B | 552 | 553 | 2.16 |
| 2.22 | | Cl | B | 536 | 537 | 2.12 |
| 2.23 | | Cl | | 576 | 577 | |
| 2.24 | | Cl | B | 538 | 539 | 2.04 |
| 2.25 | | Cl | B | 524 | 525 | 2.06 |
| 2.26 | | Cl | B | 554 | 555 | 2.00 |
| 2.27 | | Cl | B | 538 | 539 | 2.23 |
| 2.28 | | Cl | | | | |

Biological Examples

1. Activity In Vitro Against *Ctenocephalides felis* (Cat Flea)

A mixed adult population of fleas is placed in a suitably formatted 96-well plate allowing fleas to access and feed on treated blood via an artificial feeding system. In are fed on treated blood for 24 hours, after which the compound effect is recorded. Insecticidal activity is determined on the basis of the number of dead fleas recovered from the feeding system. In this test the following examples showed more than 80% (EC$_{80}$) efficacy at 100 ppm: Compound 1.1-1.3, 1.5, 1.6, 1.8, 1.12, 1.18, 1,20, 1.21, 1.26, 1.28, 1.30, 1.32, 1.36-1.39, 1.44, 1.51, 1.55-1.58, 2.1-2.22 and 2.24-2.28.

2, Activity In Vitro Against *Rhipicephalus sanguineus* (Dog Tick)

A clean adult tick population is used to seed a suitably formatted 96-well plate containing the test substances to be evaluated for antiparasitic activity. Each compound is tested by serial dilution in order to determine its minimal effective dose (MED). Ticks are left in contact with the test compound for 10 minutes and are then incubated at 28° C. and 80% relative humidity for 7 days, during which the test compound effect is monitored. Acaricidal activity is confirmed if adult ticks are dead.

In this test the following examples showed more than 80% (EC$_{80}$) efficacy at 640 ppm: 1.1-1.3, 1.5, 1.6, 1.8, 1.12, 1.28, 1.30, 1.32, 1.36-1.39, 1.44, 1.55-1.58, 2.1-2.4, 2.6-2.22 and 2.24-2.27.

3. Activity In Vivo Against *Rhipicephalus sanguineus* Nymphs on Mongolian Gerbils (*Meriones unguiculatus*) (per Oral Application)

One day before treatment, gerbils are infested with nymphs of *R. sanguineus*. On day 0, the animals are treated orally by gavage with the test compound formulated at a given dose. Ticks are left on the animals until full repletion. Seven days after infestation nymphs dropped off fully engorged are collected and counted. Efficacy in killing is expressed as a tick number reduction in comparison with a placebo treated group, using the Abbot's formula. In this test the following examples showed more than 90% (EC$_{90}$) efficacy at 100 mg/kg: 1.2, 2.1.

4. Activity In Vivo Against *Rhipicephalus sanguineus* Nymphs on Mongolian Gerbils (*Meriones unguiculatus*) (Spray Application)

On day 0, gerbils are treated with the test compound at a given dose by spray application. On day +1 (+2), the animals are infested with nymphs of *R. sanguineus*. Ticks are left on the animals until full repletion. Seven days after infestation nymphs dropped off fully engorged are collected and counted. Efficacy in killing is expressed as a tick number reduction in comparison with a placebo treated group, using the Abbot's formula. In this test the following examples showed more than 80% (EC$_{80}$) efficacy at 10 mg/kg: 1.6, 1.36, 1.55, 1.56, 2.1, 2.7, 2.8, 2.11, 2.14 and 2.15.

5. Activity In Vivo Against *Ctenocephalides felis* (Cat Flea) on Mongolian Gerbils (*Meriones unguiculatus*) (Spray Application)

On day 0, gerbils are treated with the test compound at a given dose by spray or spot-on application. On day +1, the animals are infested with a mixed adult population of cat fleas. Evaluation of efficacy is performed 24 h and 48 h infestation by counting the numbers of live fleas recovered from the gerbils. Efficacy is expressed as comparison with a placebo treated group using the Abbot's formula.

In this test the following examples showed more than 80% (EC$_{80}$) efficacy at 100 mg/kg: 1.44, 1.57, 2.1, 2.3, 2.9, 2.12 and 2.14.

What is claimed is:
1. A compound of formula

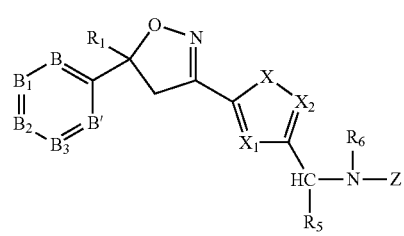

including all geometric and stereoisomers, N-oxides, S-oxides and salts thereof, wherein X is S(O)$_m$, O or NR$_5$' and X$_1$ and X$_2$ are each independently of the other CR$_3$ or N, m is an integer from 0 to 2;

R$_5$' is H, $C_1$-$C_6$-alkyl, $C_1$-$C_6$-haloalkyl, $C_1$-$C_6$-alkylcarbonyl or $C_1$-$C_6$-alkoxycarbonyl;

each R$_3$ is independently H, halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkyl-sulfinyl, $C_1$-$C_6$-haloalkylsulfinyl, $C_1$-$C_6$-alkylsulfonyl, $C_1$-$C_6$-haloalkylsulfonyl, amino, N-mono- or N,N-di-$C_1$-$C_6$-alkylamino, $C_1$-$C_6$-alkoxycarbonyl, cyano, nitro or unsubstituted or halogen-, $C_1$-$C_6$-alkyl-, $C_1$-$C_6$-haloalkyl-, $C_1$-$C_6$-alkoxy-, $C_1$-$C_6$-haloalkoxy-, amino-, cyano- or nitro-substituted phenyl, pyridyl or pyrimidyl;

B and B' are each independently a group CR$_2$'; B$_1$, B$_2$ and B$_3$ are each independently selected from the group consisting of CR$_2$' and N;

each R$_2$' is independently of the other H or R$_2$;

each R$_2$ is independently halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, N-mono- or N,N-di-$C_1$-$C_6$-alkylamino, $C_1$-$C_6$-alkoxycarbonyl, cyano (—CN) or nitro (—NO$_2$);

R$_1$ is $C_1$-$C_6$-alkyl, $C_2$-$C_6$-alkenyl, $C_2$-$C_6$-alkynyl, $C_3$-$C_6$-cycloalkyl, $C_4$-$C_7$-alkylcycloalkyl or $C_4$-$C_7$-cycloalkylalkyl, each unsubstituted or substituted with one or more substituents independently selected from R$_4$;

R$_4$ is halogen, hydroxy, $C_1$-$C_6$-alkoxy, $C_1$-$C_6$-alkylthio, $C_1$-$C_6$-alkylsulfinyl, $C_1$-$C_6$-alkylsulfonyl, cyano or nitro;

R$_5$ is H, $C_1$-$C_6$-alkyl, $C_1$-$C_6$-haloalkyl, halogen or cyano; or R$_5$ and X$_2$ together with the intermediate C-atoms form a 5- or 6-membered carbocyclic ring; or R$_5$ and X$_1$ together with the intermediate C-atoms form a 5- or 6-membered carbocyclic ring;

R$_6$ is H; $C_1$-$C_6$-alkyl, which is unsubstituted or substituted by $C_1$-$C_4$-alkoxy, cyano, phenyl, ethenyl or ethynyl; $C_2$-$C_7$-alkylcarbonyl; $C_2$-$C_7$-haloalkylcarbonyl; or $C_2$-$C_7$-alkoxycarbonyl;

Z is $C_1$-$C_6$-alkyl, a group —C(O)-Q, a group —C(S)-Q or a group —S(O)$_t$-Q; t is 1 or 2;

Q is $C_1$-$C_6$-alkoxy; $C_1$-$C_6$-haloalkoxy; $C_1$-$C_6$-alkylthio; $C_1$-$C_6$-haloalkylthio; NR$_7$R$_8$;

C(O)OR$_7$; C(O)R$_7$; $C_1$-$C_6$-alkyl which is unsubstituted or substituted by $C_3$-$C_6$-cycloalkyl, halogen, cyano, nitro, hydroxy, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, NHC(O)R$_7$, $C_1$-$C_6$-alkoxycarbonyl, sulfonamido, N-mono- or N,N, di-$C_1$-$C_4$-alkylsulfonamido, C(O)NR$_7$R$_8$, $C_2$-$C_6$-alkanoyl, unsubstituted or $C_1$-$C_2$-alkyl-, $C_1$-$C_2$-haloalkyl-, $C_1$-$C_2$-alkoxy-, $C_1$-$C_2$-haloalkoxy-, halogen-, cyano- or $C_1$-$C_4$-alkoxycarbonyl-substituted $C_6$-$C_{10}$-aryl, or unsubstituted or $C_1$-$C_2$-alkyl-, $C_1$-$C_2$-haloalkyl-, $C_1$-$C_2$-alkoxy-, $C_1$-$C_2$-haloalkoxy-, halogen-, cyano- or $C_1$-$C_4$-alkoxycarbonyl-substituted 4- to 6-membered heterocyclyl; $C_2$-$C_6$-alkenyl; $C_2$-$C_6$-alkynyl; $C_3$-$C_6$-cycloalkyl which is unsubstituted or substituted by halogen, $C_1$-$C_2$-alkyl or $C_1$-$C_2$-haloalkyl; $C_6$-$C_{10}$-aryl unsubstituted or substituted by $C_1$-$C_2$-alkyl, $C_1$-$C_2$-haloalkyl, $C_1$-$C_2$-alkoxy, $C_1$-$C_2$-haloalkoxy, halogen, cyano or $C_1$-$C_4$-alkoxycarbonyl; or 4- to 6-membered heterocyclyl unsubstituted or substituted by $C_1$-$C_2$-alkyl, $C_1$-$C_2$-haloalkyl, $C_1$-$C_2$-alkoxy, $C_1$-$C_2$-haloalkoxy, halogen, cyano or $C_1$-$C_4$-alkoxycarbonyl; and R$_7$ and R$_8$ are each independently of the other H, $C_1$-$C_6$-alkyl, $C_1$-$C_6$-haloalkyl, unsubstituted or $C_1$-$C_4$-alkyl-substituted $C_3$-$C_6$-cycloalkyl, $C_2$-$C_6$-alkenyl or $C_2$-$C_6$-alkynyl.

2. A compound according to claim 1, wherein $B_1$, $B_2$ and $B_3$ are each CR$_2$'.

3. A compound according to claim 1, wherein X is S(O)$_m$, one of $X_1$ and $X_2$ is CR$_3$ and the other one is N or independently CR$_3$, wherein R$_3$ is each independently H or $C_1$-$C_2$-alkyl, and m is an integer from 0 to 2.

4. A compound according to claim 1, wherein R$_1$ is $C_1$-$C_3$-haloalkyl, in particular CF$_3$.

5. A compound according to claim 1, wherein R$_1$ is CF$_3$.

6. A compound according to claim 1 of formula

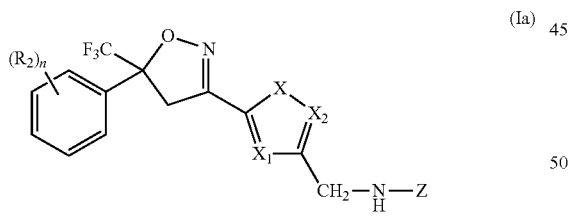

(Ia)

wherein R$_2$, X, $X_1$, $X_2$ and Z are as defined in claim 1 and n is an integer of from 1 to 3.

7. A compound according to claim 6, wherein Z is a group —C(O)-Q.

8. A compound according to claim 7, wherein Q is straight-chain or branched $C_1$-$C_4$-alkyl, which is each unsubstituted or substituted by $C_3$-$C_6$-cycloalkyl, halogen, cyano, hydroxy, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-alkylsulfonyl, $C_1$-$C_2$-alkylcarbonylamino, $C_1$-$C_2$-haloalkylcarbonylamino or dioxolanyl; unsubstituted or methyl-substituted $C_3$-$C_6$-cycloalkyl; phenyl, which is unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano or $C_1$-$C_4$-alkoxycarbonyl; thienyl, furyl, oxazolyl, thiazolyl, pyridyl or pyrimidinyl, which are each unsubstituted or substituted by $C_1$-$C_2$-alkyl, $C_1$-$C_2$-haloalkyl or $C_1$-$C_4$-alkoxycarbonyl; 1,3-dioxan-2-yl or 1,3-dioxolan-2-yl; or pyrrolidinyl, tetrahydrofuranyl, tetrahydrothiophenyl, piperidinyl, piperazinyl, morpholinyl, tetrahydropyranyl or thianyl which are each unsubstituted or substituted by $C_1$-$C_2$-alkyl, $C_1$-$C_2$-haloalkyl or $C_1$-$C_4$-alkoxycarbonyl.

9. A compound according to claim 7, wherein Q is straight-chain or branched $C_1$-$C_4$-alkyl, cyclopropyl, cyclobutyl, halo-$C_1$-$C_3$-alkyl, cyano-$C_1$-$C_2$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulfinyl-$C_1$-$C_2$-alkyl, $C_1$-$C_2$-alkylsulfonyl-$C_1$-$C_2$-alkyl, $C_1$-$C_2$-haloalkylcarbonylamino-$C_1$-$C_2$-alkyl, tetrahydrofuranyl or 2-(1,3-dioxolan-2yl)-n-propyl.

10. A compound of formula (Ia) according to claim 6, wherein n is an integer from 1 to 3; each R$_2$ is independently selected from the group consisting of halogen, $C_1$-$C_6$-haloalkyl, $C_1$-$C_6$-haloalkoxy and cyano; X is S(O)$_m$, O or NR$_5$'; m is an integer from 0 to 2; R5' is H or $C_1$-$C_2$-alkyl; one of $X_1$ and $X_2$ is CR$_3$' and the other one is N or independently CR$_3$'; R$_3$' is H or $C_1$-$C_2$-alkyl; Z is a group —S(O)$_2$-$C_1$-$C_2$-alkyl or a group —C(O)-Q; and Q is straight-chain or branched $C_1$-$C_4$-alkyl, which is each unsubstituted or substituted by $C_3$-$C_6$-cycloalkyl, halogen, cyano, $C_1$-$C_4$-alkoxy, $C_1$-$C_2$-haloalkoxy, $C_1$-$C_4$-alkylthio, $C_1$-$C_2$-haloalkylthio, $C_1$-$C_4$-alkylsulfinyl, $C_1$-$C_4$-alkylsulfonyl, $C_1$-$C_2$-alkylcarbonylamino, $C_1$-$C_2$-haloalkylcarbonylamino or dioxolanyl; unsubstituted or methyl-substituted $C_3$-$C_6$-cycloalkyl; phenyl, which is unsubstituted or substituted by halogen, $C_1$-$C_2$-alkyl, $C_1$-$C_2$-haloalkyl, $C_1$-$C_2$-alkoxy, $C_1$-$C_2$-haloalkoxy, cyano or $C_1$-$C_4$-alkoxycarbonyl; thienyl, furyl, oxazolyl, thiazolyl, pyridyl or pyrimidinyl, which are each unsubstituted or substituted by $C_1$-$C_2$-alkyl, $C_1$-$C_2$-haloalkyl or $C_1$-$C_4$-alkoxycarbonyl; or pyrrolidinyl, tetrahydrofuranyl, tetrahydrothiophenyl, piperidinyl, piperazinyl, morpholinyl, tetrahydropyranyl or thianyl which is each unsubstituted or substituted by $C_1$-$C_2$-alkyl, $C_1$-$C_2$-haloalkyl or $C_1$-$C_4$-alkoxycarbonyl.

11. A compound of formula

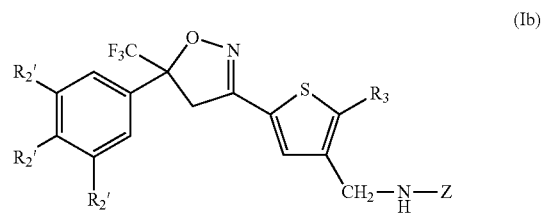

(Ib)

including all geometric and stereoisomers, N-oxides, and salts thereof, wherein the radicals R$_2$' are each independently of the other H, halogen or trifluoromethyl, subject to the proviso that at least 2 radicals R$_2$' are not H; R$_3$ is hydrogen or methyl; Z is a radical —C(O)-Q; and Q is straight-chain or branched $C_1$-$C_4$-alkyl, cyclopropyl, cyclobutyl, $C_1$-$C_3$-haloalkyl, cyano-$C_1$-$C_2$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulfinyl-$C_1$-$C_2$-alkyl, $C_1$-$C_2$-alkylsulfonyl-$C_1$-$C_2$-alkyl, $C_1$-$C_2$-haloalkyl-carbonylamino-$C_1$-$C_2$-alkyl, tetrahydrofuranyl or 2-(1,3-dioxolan-2yl)-n-propyl.

12. A compound of formula (Ib) according to claim 11, which is

N-{5-[5-(3,5-dichloro-phenyl)-5-trifluoromethyl-4,5-dihydro-isoxazol-3-yl]-2-methyl-thiophen-3-ylmethyl}-propionamide;

N-{5-[5-(3,4,5-trichloro-phenyl)-5-trifluoromethyl-4,5-dihydro-isoxazol-3-yl]-2-methyl-thiophen-3-ylmethyl}-propionamide;

cyclopropanecarboxylic acid {2-methyl-5-[5-(3,5-dichloro-phenyl)-5-trifluoromethyl-4,5-di-hydro-isoxazol-3-yl]-thiophen-3-ylmethyl}-amide;

cyclopropanecarboxylic acid {2-methyl-5-[5-(3,4,5-trichloro-phenyl)-5-trifluoromethyl-4,5-di-hydro-isoxazol-3-yl]-thiophen-3-ylmethyl}-amide;

tetrahydro-furan-3-carboxylic acid {2-methyl-5-[5-(3,5-dichloro-phenyl)-5-trifluoromethyl-4,5-dihydro-isoxazol-3-yl]-thiophen-3-ylmethyl}-amide; or tetrahydro-furan-3-carboxylic acid {2-methyl-5-[5-(3,4,5-trichloro-phenyl)-5-trifluoromethyl-4,5-dihydro-isoxazol-3-yl]-thiophen-3-ylmethyl}-amide.

13. A compound of formula

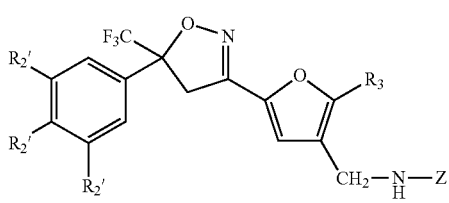

(Ic)

including all geometric and stereoisomers, N-oxides, and salts thereof, wherein the radicals $R_2'$ are each independently of the other H, halogen or trifluoromethyl, subject to the proviso that at least 2 radicals $R_2'$ are not H; $R_3$ is hydrogen or methyl; Z is a radical —C(O)-Q; and Q is straight-chain or branched $C_1$-$C_4$-alkyl, cyclopropyl, cyclobutyl, $C_1$-$C_3$-haloalkyl, cyano-$C_1$-$C_2$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulfinyl-$C_1$-$C_2$-alkyl, $C_1$-$C_2$-alkylsulfonyl-$C_1$-$C_2$-alkyl, $C_1$-$C_2$-haloalkyl-carbonylamino-$C_1$-$C_2$-alkyl, tetrahydrofuranyl or 2-(1,3-dioxolan-2yl)-n-propyl.

14. A compound of formula (Ic) according to claim 13, which is

N-{5-[5-(3,5-dichloro-phenyl)-5-trifluoromethyl-4,5-dihydro-isoxazol-3-yl]-2-methyl-furan-3-ylmethyl}-propionamide;

N-{5-[5-(3,4,5-trichloro-phenyl)-5-trifluoromethyl-4,5-dihydro-isoxazol-3-yl]-2-methyl-furan-3-ylmethyl}-propionamide;

cyclopropanecarboxylic acid {2-methyl-5-[5-(3,5-dichloro-phenyl)-5-trifluoromethyl-4,5-di-hydro-isoxazol-3-yl]-furan-3-ylmethyl}-amide;

cyclopropanecarboxylic acid {2-methyl-5-[5-(3,4,5-trichloro-phenyl)-5-trifluoromethyl-4,5-di-hydro-isoxazol-3-yl]-furan-3-ylmethyl}-amide;

tetrahydro-furan-3-carboxylic acid {2-methyl-5-[5-(3,5-dichloro-phenyl)-5-trifluoromethyl-4,5-dihydro-isoxazol-3-yl]-furan-3-ylmethyl}-amide; or tetrahydro-furan-3-carboxylic acid {2-methyl-5-[5-(3,4,5-trichloro-phenyl)-5-trifluoromethyl-4,5-dihydro-isoxazol-3-yl]-furan-3-ylmethyl}-amide.

15. A composition for the control of parasites, comprising as active ingredient at least one compound of the formula (I) according to claim 1, in addition to a carrier and/or a dispersant.

16. A composition for the control of parasites, comprising as active ingredient at least one compound of formula (Ib) according to claim 11, in addition to a carrier and/or a dispersant.

17. A composition for the control of parasites, comprising as active ingredient at least one compound of formula (Ic) according to claim 13, in addition to a carrier and/or a dispersant.

18. A method of controlling parasites in and on vertebrates, which comprises applying to the vertebrates a pharmaceutically effective amount of at least one compound of formula (I) according to claim 1.

19. A method of controlling parasites in and on vertebrates, which comprises applying to the vertebrates a pharmaceutically effective amount of at least one compound of formula (Ia) according to claim 6.

20. A method of controlling parasites in and on vertebrates, which comprises applying to the vertebrates a pharmaceutically effective amount of at least one compound of formula (Ib) according to claim 11.

21. A method of controlling parasites in and on vertebrates, which comprises applying to the vertebrates a pharmaceutically effective amount of at least one compound of formula (Ic) according to claim 13.

* * * * *